(12) United States Patent
Yoo et al.

(10) Patent No.: US 12,256,880 B2
(45) Date of Patent: Mar. 25, 2025

(54) SHOE MANAGEMENT APPARATUS

(71) Applicant: LG ELECTRONICS INC., Seoul (KR)

(72) Inventors: Hyunsun Yoo, Seoul (KR); Jeong Guen Choi, Seoul (KR); Joohyeon Oh, Seoul (KR); Jae Myung Lim, Seoul (KR); Byoungjoon Han, Seoul (KR); Sang Yoon Lee, Seoul (KR); Hyunju Kim, Seoul (KR); Jeaseok Seong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 785 days.

(21) Appl. No.: 17/356,336

(22) Filed: Jun. 23, 2021

(65) Prior Publication Data
US 2021/0401263 A1 Dec. 30, 2021

(30) Foreign Application Priority Data

Jun. 24, 2020 (KR) ......................... 10-2020-0077410
Jun. 24, 2020 (KR) ......................... 10-2020-0077411
(Continued)

(51) Int. Cl.
*A47L 23/02* (2006.01)
*A47B 61/04* (2006.01)
(Continued)

(52) U.S. Cl.
CPC .............. *A47L 23/02* (2013.01); *A47B 61/04* (2013.01); *A47L 23/205* (2013.01); *A61L 2/07* (2013.01);
(Continued)

(58) Field of Classification Search
None
See application file for complete search history.

(56) References Cited

U.S. PATENT DOCUMENTS 3,802,021 A 4/1974 Schulz
5,369,892 A * 12/1994 Dhaemers ............... F26B 21/00
34/224
(Continued)

FOREIGN PATENT DOCUMENTS

CN 104687789 A 6/2015
CN 105686783 A 6/2016
(Continued)

OTHER PUBLICATIONS

Korean Notice of Allowance for Korean Application No. 10-2021-0030923, dated Sep. 9, 2024.
(Continued)

*Primary Examiner* — Holly Kipouros
(74) *Attorney, Agent, or Firm* — Birch, Stewart, Kolasch & Birch, LLP

(57) ABSTRACT

A shoe management apparatus includes a first management apparatus, including a first inner space and an electric compartment disposed below the first inner space for dehumidifying air introduced into the electric compartment, and removing foreign matter from the shoes stored in the first inner space; and a second management apparatus disposed above the first management apparatus, including a second inner space for storing a shoe, and for adjusting humidity of the second inner space using air discharged from the electric compartment.

19 Claims, 24 Drawing Sheets

(30) Foreign Application Priority Data

| | | | |
|---|---|---|---|
| Jun. 24, 2020 | (KR) | ........................ | 10-2020-0077412 |
| Jun. 24, 2020 | (KR) | ........................ | 10-2020-0077413 |
| Jun. 24, 2020 | (KR) | ........................ | 10-2020-0077414 |
| Jun. 24, 2020 | (KR) | ........................ | 10-2020-0077415 |
| Jun. 24, 2020 | (KR) | ........................ | 10-2020-0077417 |
| Dec. 8, 2020 | (KR) | ........................ | 10-2020-0170566 |
| Mar. 9, 2021 | (KR) | ........................ | 10-2021-0031065 |

(51) Int. Cl.
  *A47L 23/20* (2006.01)
  *A61L 2/07* (2006.01)
(52) U.S. Cl.
  CPC ....... *A47L 2601/04* (2013.01); *A47L 2601/20* (2013.01)

(56) References Cited

U.S. PATENT DOCUMENTS

| | | | | |
|---|---|---|---|---|
| 2005/0109643 | A1* | 5/2005 | Huang | .................... A61L 2/202 |
| | | | | 206/278 |
| 2009/0038096 | A1 | 2/2009 | Hollander | |
| 2009/0320314 | A1 | 12/2009 | Jo et al. | |
| 2010/0040515 | A1* | 2/2010 | Lovelace | ................. A61L 2/202 |
| | | | | 220/524 |
| 2021/0071346 | A1 | 3/2021 | Lee et al. | |
| 2021/0071950 | A1* | 3/2021 | Ohnari | .................. F26B 25/008 |

FOREIGN PATENT DOCUMENTS

| | | | |
|---|---|---|---|
| CN | 106073685 | A | 11/2016 |
| CN | 109106086 | A | 1/2019 |
| CN | 209171826 | U | 7/2019 |
| CN | 209825741 | U | 12/2019 |
| JP | 2-6543 | U | 1/1990 |
| JP | 5-192291 | A | 8/1993 |
| JP | 9-253595 | A | 9/1997 |
| JP | 11-103941 | A | 4/1999 |
| JP | 2002-177374 | A | 6/2002 |
| JP | 2010-119609 | A | 6/2010 |
| KR | 20-1999-0009039 | U | 3/1999 |
| KR | 20-0165450 | Y1 | 2/2000 |
| KR | 20-0187262 | Y1 | 7/2000 |
| KR | 20-0253977 | Y1 | 11/2001 |
| KR | 20-0284482 | Y1 | 8/2002 |
| KR | 20-0286953 | Y1 | 8/2002 |
| KR | 20-0307594 | Y1 | 3/2003 |
| KR | 20-0357295 | Y1 | 7/2004 |
| KR | 10-2004-0070545 | A | 8/2004 |
| KR | 20-0381792 | Y1 | 4/2005 |
| KR | 10-2006-0060230 | A | 6/2006 |
| KR | 10-0590794 | B1 | 6/2006 |
| KR | 10-0625104 | B1 | 9/2006 |
| KR | 20-0426182 | Y1 | 9/2006 |
| KR | 20-0291502 | Y1 | 11/2006 |
| KR | 20-0431598 | Y1 | 11/2006 |
| KR | 10-2008-0006908 | A | 1/2008 |
| KR | 10-2008-0105499 | A | 12/2008 |
| KR | 10-0996307 | B1 | 11/2010 |
| KR | 10-1059224 | B1 | 8/2011 |
| KR | 10-2011-0106834 | A | 9/2011 |
| KR | 10-202-0059781 | A | 6/2012 |
| KR | 10-2012-0059781 | A | 6/2012 |
| KR | 10-2012-0119542 | A | 10/2012 |
| KR | 10-1364529 | B1 | 2/2014 |
| KR | 10-2014-0106818 | A | 9/2014 |
| KR | 10-2014-0107876 | A | 9/2014 |
| KR | 10-1500909 | B1 | 3/2015 |
| KR | 10-2015-0086056 | A | 7/2015 |
| KR | 10-2015-0117430 | A | 10/2015 |
| KR | 10-2015-0123493 | A | 11/2015 |
| KR | 10-2015-0129426 | A | 11/2015 |
| KR | 10-1572229 | B1 | 11/2015 |
| KR | 10-1581441 | B1 | 12/2015 |
| KR | 10-2017-0024363 | A | 3/2017 |
| KR | 10-2017-0039412 | A | 4/2017 |
| KR | 10-1737829 | B1 | 5/2017 |
| KR | 10-2018-0015897 | A | 2/2018 |
| KR | 10-2018-0054004 | A | 5/2018 |
| KR | 20-2018-0001463 | U | 5/2018 |
| KR | 10-2019-0003274 | A | 1/2019 |
| KR | 10-1938421 | B1 | 1/2019 |
| KR | 10-2019-0029009 | A | 3/2019 |
| KR | 10-2008104 | B1 | 8/2019 |
| KR | 10-2019-0128460 | A | 11/2019 |
| KR | 10-2020-0002725 | A | 1/2020 |
| KR | 10-2020-0037035 | A | 4/2020 |
| KR | 10-2116945 | B1 | 5/2020 |
| WO | WO2010/093173 | A2 | 8/2010 |

OTHER PUBLICATIONS

Korean Office Action for Korean Application No. 10-2021-0030921, dated Aug. 8, 2024.
Korean Office Action for Korean Application No. 10-2021-0030922, dated Sep. 9, 2024.
Korean Office Action for Korean Application No. 10-2021-0030924, dated Sep. 9, 2024.
Korean Office Action for Korean Application No. 10-2021-0030926, dated Sep. 11, 2024.
Korean Office Action for Korean Application No. 10-2021-0030971, dated Oct. 25, 2024.
Korean Office Action for Korean Application No. 10-2021-0030972, dated Oct. 25, 2024.
Korean Office Action for Korean Application No. 10-2021-0030973, dated Oct. 25, 2024.
Korean Notice of Allowance for Korean Application No. 10-2021-0031058, dated Nov. 6, 2024.
Korean Office Action for Korean Application No. 10-2021-0031056, dated Nov. 6, 2024.

* cited by examiner

SHOE MANAGEMENT APPARATUS

CROSS-REFERENCE TO RELATED APPLICATIONS

This application claims priority to and the benefit of Korean Patent Application No. 10-2020-0077410, filed on Jun. 24, 2020, No. 10-2020-0077411, filed on Jun. 24, 2020, Korean Patent Application No. 10-2020-77412, filed on Jun. 24, 2020, Korean Patent Application No. 10-2020-0077413, filed on Jun. 24, 2020, Korean Patent Application No. 10-2020-77414, filed on Jun. 24, 2020, Korean Patent Application No. 10-2020-0077415, filed on Jun. 24, 2020, Korean Patent Application No. 10-2020-0077417, filed on Jun. 24, 2020, Korean Patent Application No. 10-2020-0170566, filed on Dec. 8, 2020 and Korean Patent Application No. 10-2021-0031065, filed on Mar. 9, 2021, the disclosures of which are incorporated herein by reference in their entirety in to the present application.

BACKGROUND OF THE INVENTION

1. Field of the Invention

The present disclosure relates to a shoe management apparatus which can perform at least one function selected from among storage, sterilization, and decontamination of shoes.

2. Description of the Background Art

Generally, a shoe rack installed in an entrance room of a building is used to hold and organize various types of shoes.

However, when shoes wet with water or sweat are stored in a shoe rack, the humidity inside the shoe rack increases, causing deterioration and reduction in lifespan of all shoes stored therein. In particular, with increasing demand for high-end shoes in recent years, interest is growing for an apparatus that can properly manage and maintain shoes to extend lifespan of the shoes.

In addition, shoes are generally used for outdoor activities and thus can be easily contaminated with dust, bacteria, and viruses. Therefore, it is important from the viewpoint of hygiene for households to frequently perform sterilization or decontamination of shoes.

SUMMARY OF THE INVENTION

Embodiments of the present disclosure provide a shoe management apparatus, which can store shoes for a long time, while providing removal of contaminants from the shoes.

Embodiments of the present disclosure provide a shoe management apparatus that can be built-in in an entrance room of a building while providing total care for shoes.

The above and other objects and advantages of the present disclosure will become apparent from the detailed description of the following embodiments in conjunction with the accompanying drawings. In addition, it will be readily understood that the objects and advantages of the present disclosure can be realized by features set forth in the appended claims or combinations thereof.

In accordance with one aspect of the present disclosure, a shoe management apparatus has a structure in which an electric compartment, a first inner space for intensive care for shoes, and a second inner space for storing shoes (e.g., for a long time) are sequentially stacked from bottom to top.

In an embodiment, the two inner spaces for performing different functions may share the electric compartment to provide care for shoes placed therein (i.e., to clean shoes placed therein).

In an embodiment, a water container, a main fan, and a housing constituting the electric compartment may be sequentially arranged from one side of the electric compartment to the other side thereof.

In accordance with another aspect of the present disclosure, a shoe management apparatus includes a first management apparatus and a second management apparatus disposed on an upper surface of the first management apparatus. The first management apparatus includes an electric compartment dehumidifying air introduced thereinto. In addition, the first management apparatus is formed on an upper side of the electric compartment with a first inner space for storing shoes and is configured to remove foreign matter from the shoes stored in the first inner space. The second management apparatus is formed with a second inner space for storing shoes. The second management apparatus is configured to adjust humidity of the second inner space using air discharged from the electric compartment.

In an embodiment, the first management apparatus may include a first cabinet and a first partition. The first cabinet may define an exterior of the first management apparatus, a space for the electric compartment, and the first inner space. The first partition may divide the first inner space from side to side.

In an embodiment, the electric compartment may include a main fan drawing in air by creating a vacuum and discharging the drawn-in air. In addition, the electric compartment may include a housing disposed at one lateral side of the main fan and configured to dehumidify air therein and to allow the dehumidified air to be drawn into the main fan. In addition, the electric compartment may include a steam generator disposed at the one lateral side of the main fan and generating steam to be supplied to the first inner space by heating water. In addition, the electric compartment may include a water supply container disposed at the other lateral side of the main fan to supply water to the steam generator, the water supply container being detachably coupled to the first cabinet. In addition, the electric compartment may include a drain container disposed on the other lateral side of the main fan to collect moisture removed in the housing.

In an embodiment, the electric compartment may further include an air distributor receiving the air discharged from the main fan and distributing the received air to the first inner space and to the second inner space.

In an embodiment, the first management apparatus may further include a first exhaust port disposed at a rear upper end of the first cabinet and allowing the air discharged from the main fan to be diffusely discharged therethrough. In addition, the first management apparatus may further include a longitudinal connection pipe connected between the main fan and the first exhaust port and guiding the air discharged from the main fan to the first exhaust port.

In an embodiment, the longitudinal connection pipe may be at least partially disposed inside the first partition.

In an embodiment, the first management apparatus may further include an inner panel disposed at a rear upper portion of the first inner space with an upper end of the inner panel located ahead of a lower end of the inner panel. In addition, the first management apparatus may further include a blower fan disposed between the inner panel and an inner surface of the first cabinet to force air to the first inner space.

In an embodiment, the first management apparatus may perform at least one operation selected from contaminant removal, sterilization, deodorization, dehumidification, drying, and coating for the shoes stored in the first inner space.

In an embodiment, the second management apparatus may include a second cabinet defining an exterior of the second management apparatus and the second inner space. In addition, the second management apparatus may include a second exhaust port disposed at a rear bottom of the second inner space and configured to receive the air discharged from the electric compartment and guide the received air to the second inner space.

In an embodiment, the second management apparatus may further include at least one second partition dividing the second inner space from top to bottom. The at least one second partition has a rear end, and at least some part of the rear end is spaced apart from an inner surface of the second cabinet.

In an embodiment, the second management apparatus may further include a circulation filter disposed on an inner side surface of the second cabinet, having a wider upper opening and a narrower lower opening, and configured to remove contamination from air introduced thereinto.

In accordance with a further aspect of the present disclosure, a shoe management apparatus includes an electric compartment, a first cabinet, and a second cabinet. The electric compartment dehumidifies air introduced thereinto, generates steam by heating water, and discharges the dehumidified air and the steam. The first cabinet houses the electric compartment and is formed on an upper side of the electric compartment with a first inner space for storing shoes, the first inner space being supplied with the air and the steam discharged from the electric compartment. The second cabinet is disposed on an upper surface of the first cabinet and is formed with a second inner space for storing shoes, the second inner space being supplied with the air discharged from the electric compartment.

In an embodiment, the shoe management apparatus may further include a first exhaust port disposed at a rear upper end of the first cabinet and allowing the air discharged from the electric compartment to be discharged therethrough. In addition, the shoe management apparatus may further include a second exhaust port disposed at a rear bottom of the second cabinet and guiding the air discharged from the first exhaust port to the second inner space.

In accordance with yet another aspect of the present disclosure, a shoe management apparatus includes: an electric compartment forcing a fluid to flow; a first management apparatus disposed on an upper side of the electric compartment and defining a first inner space for storing shoes, the first inner space being supplied with the fluid; and a second management apparatus disposed on an upper surface of the first management apparatus and defining a second inner space for storing shoes, the second inner space being supplied with the fluid.

In an embodiment, the first management apparatus may perform at least one operation selected from among contaminant removal, sterilization, deodorization, dehumidification, drying, and coating for the shoes stored in the first inner space.

In an embodiment, the second management apparatus may perform at least one operation selected from among of sterilization, ventilation, and humidity control of the second inner space.

In an embodiment, the shoe management apparatus may further include: a fluid path extending through the first management apparatus and guiding the fluid discharged from the electric compartment to the second inner space.

The shoe management apparatus according to the present disclosure can store shoes for a long time while providing removal of contaminants from the shoes.

In addition, the shoe management apparatus according to the present disclosure can be built-in in an entrance room of a building while providing total care for shoes.

The above and other effects of the present disclosure will become apparent from the following detailed description of the present disclosure.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

Figure 1:
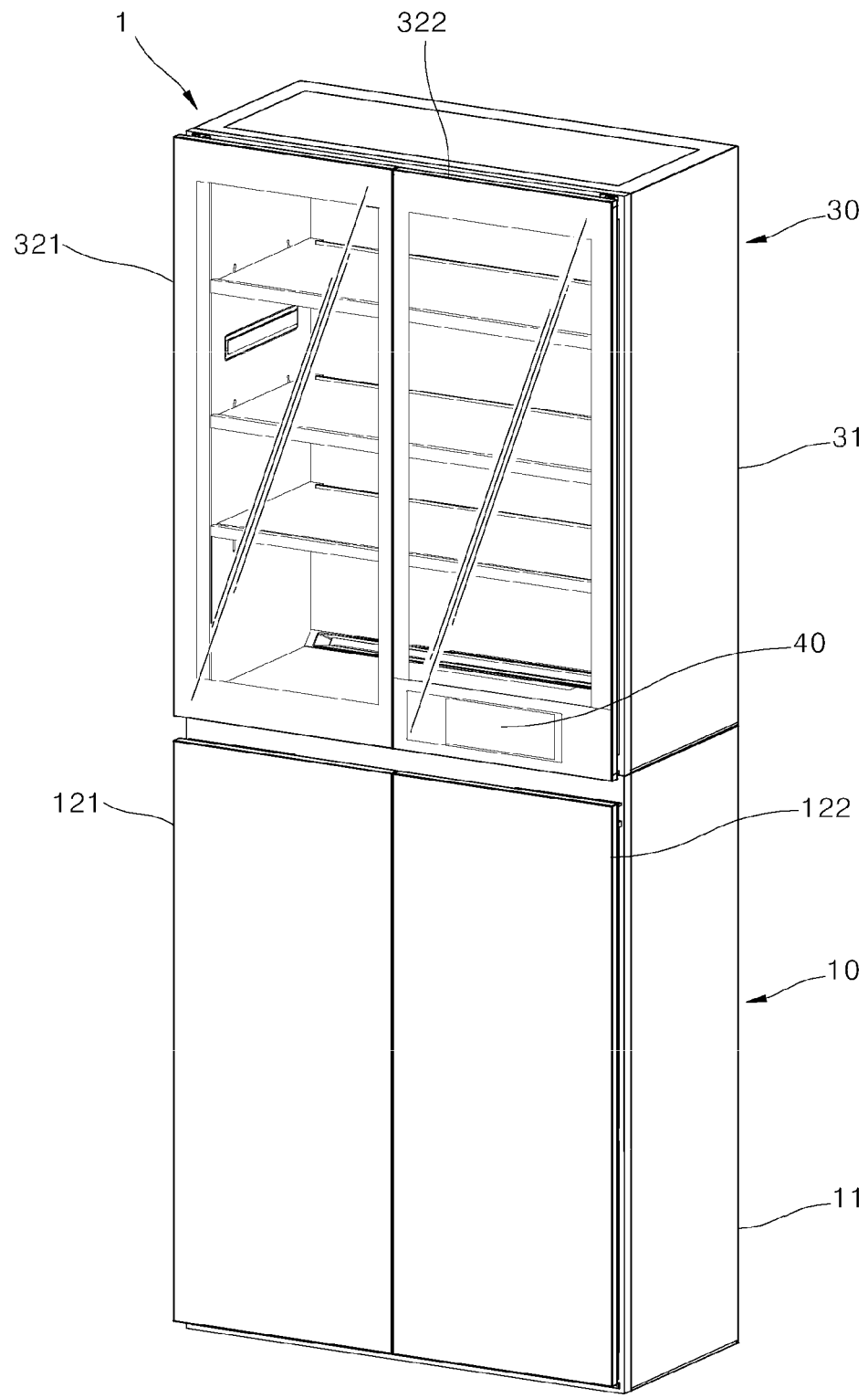
FIG. 1 is a perspective view of a shoe management apparatus according to an embodiment of the present disclosure.

Reference will now be made in detail to various embodiments, examples of which are illustrated in the accompanying drawings such that the present disclosure can be easily implemented by those skilled in the art. Description of known functions and constructions which may unnecessarily obscure the subject matter of the present disclosure will be omitted. Like components will be denoted by like reference numerals throughout the specification.

It will be understood that, although the terms "first", "second", and the like may be used herein to describe various elements and the like, these elements should not be limited by these terms. These terms are only used to distinguish one element from another element. Thus, a first element discussed below could be termed a second element, or vice versa, without departing from the scope of the present disclosure.

It will be understood that when a component is referred to as being disposed "at an upper (lower) portion of" or "on (or "under") another component, it can be directly formed to adjoin an upper surface ("a lower surface") of the other component, or intervening component(s) may also be interposed therebetween.

In addition, when a certain component is referred to as being "connected to", "coupled to" or "joined to" another component, these components may be directly connected to, coupled to or joined to each other or through another component, or intervening component(s) may also be "interposed" therebetween.

As used herein, the singular forms, "a," "an," and "the" are intended to include the plural forms as well, unless the context clearly indicates otherwise. Moreover, the terms "comprises," "comprising," "includes," and/or "including," when used in this specification, should not be construed to mean that a process, method, article, or apparatus comprising a list of elements or steps necessarily comprises all the elements or all the steps. Thus, such a process, method, article, or apparatus may be free from some of the elements or the steps, or may further include one or more other elements or steps.

Hereinafter, a shoe management apparatus according to some exemplary embodiments of the present disclosure will be described.

FIG. 1 is a perspective view of a shoe management apparatus 1 according to an embodiment of the present disclosure. The shoe management apparatus 1 may include a first management apparatus 10 and a second management apparatus 30. The first management apparatus 10 may include a first cabinet 11, a 1st first door 121, and a 2nd first door 122, and the second management apparatus 30 may include a second cabinet 31, a 1st second door 321, and a 2nd second door 322. The shoe management apparatus 1 may further include a display unit 40. The display unit 40 may be an electronic visual display, such as an LCD, TFT-LCD, OLED, a flexible display and a three-dimensional display.

The first management apparatus 10 may be disposed at a lower portion of the shoe management apparatus 1. The first management apparatus 10 may perform at least one operation selected from among removal of contaminants, such as dust, sterilization, deodorization, dehumidification, drying, and coating for shoes placed therein. Here, the sterilization operation may include at least one selected from among ultraviolet (UV) sterilization and steam sterilization. UV sterilization may be an operation of irradiating the shoes with short-wave UV rays having a wavelength of about 100 nm to 280 nm. Steam sterilization may be an operation of sterilizing the shoes using steam generated by heating water. The steam may be generated by heating water to 100° C. In addition, the generated steam may have a temperature of 40° C. to 50° C.

The first management apparatus 10 may be an apparatus that performs at least two of the aforementioned operations (that is, contaminant removal, sterilization, deodorization, dehumidification, drying, and coating) for a relatively short period of time in order to remove contamination of shoes placed therein. For example, the first management apparatus may sequentially perform removal of contaminants, such as dust, from surfaces of the shoes placed therein, sterilization and deodorization using the short-wave UV rays and a photocatalyst, sterilization using steam, dehumidification and drying, and coating for providing repellency to water for a predetermined period of time (for example, 40 minutes). That is, the first management apparatus 10 may be referred to as an "intensive care apparatus".

The first cabinet 11 of the first management apparatus 10 may define an exterior of the first management apparatus 10. The first cabinet 11 may be provided in the form of a cuboid open at a front thereof.

The 1st first door 121 and the 2nd first door 122 of the first management apparatus 10 may be disposed at the front of the first cabinet 11.

The second management apparatus 30 may be disposed on (so as to directly contact) an upper surface of the first management apparatus 10. The second management apparatus 30 may perform at least one operation selected from among sterilization, ventilation, and humidity control of a space in which shoes are placed. Here, the sterilization operation may be performed using the short-wave ultraviolet rays described above or a photocatalytic filter.

The second management apparatus 30 may be an apparatus that constantly performs operations necessary for preventing deterioration of shoes stored therein. That is, the second management apparatus 30 may be referred to as a "constant management apparatus" or "light care apparatus".

The second cabinet 31 of the second management apparatus 30 may define an exterior of the second management apparatus 30. The second cabinet 31 may be provided in the form of a cuboid open at a front thereof.

The 1st second door 321 (that is, a first upper door) and the 2nd second door 322 of the second management apparatus may be disposed at the front of the second cabinet 31.

The display unit 40 may display a current operating state, abnormality, or the like of the shoe management apparatus 1. The display unit 40 may be disposed at a lower portion of the 2nd second door 322.

For convenience of description, a side or portion of the shoe management apparatus 1 at which the doors 121, 122, 321, 322 are disposed is defined as "front" and the other side or portion of the shoe management apparatus 1 is defined as "rear".

Figure 2:
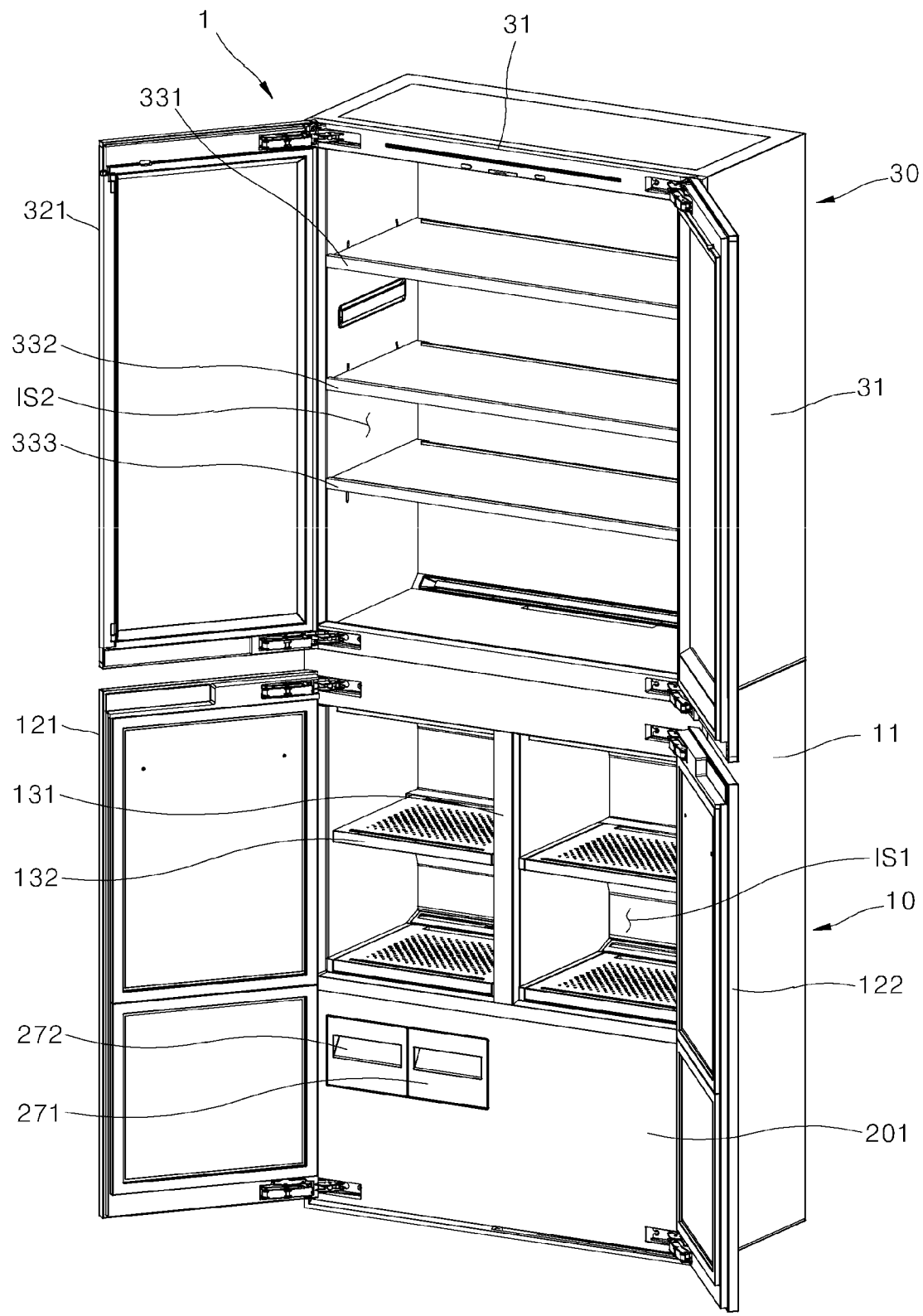
FIG. 2 is a front view of the shoe management apparatus according to an embodiment of the present disclosure shown in FIG. 1, with doors opened.

FIG. 2 is a front view of the shoe management apparatus 1 according to an embodiment of the present disclosure shown in FIG. 1, with the doors opened.

The first management apparatus 10 may be formed at an upper portion thereof with a first inner space IS1 for storing shoes and may include an electric compartment disposed under the first inner space IS1. An electric compartment front panel 201 may be disposed at a front of a space for the electric compartment. That is, the first cabinet 11 may define the first inner space IS1 and the space for the electric compartment, and the front of the electric compartment may be covered by the electric compartment front panel 201.

The space for the electric compartment may contain devices for dehumidifying air in the electric compartment, devices for discharging the dehumidified air to the first inner space IS1 and a second inner space IS2 of the second management apparatus 30, a water supply container 271 of the second management apparatus 30, and a drain container 272 of the second management apparatus 30.

The first management apparatus 10 may include at least one first partition dividing the first inner space IS1 into multiple compartments. The first partition may include a partition dividing the first inner space IS1 from side to side.

As in this embodiment, the first inner space IS1 may be divided by a 1st first partition 131, a 2nd first partition 132, and a 3rd first partition 133. The 1st first partition 131 may divide the first inner space IS1 from side to side. The 1st first partition 131 may be disposed at a center of the first inner space IS1 with reference to the side-to-side direction. Each of the 2nd first partition 132 and the 3rd first partition 133 may divide the first inner space IS1 from top to bottom.

The second management apparatus 30 may be formed with a second inner space IS2 for storing shoes. That is, the second cabinet 31 may define the second inner space IS2 for storing shoes.

The second management apparatus 30 may include at least one second partition dividing the second inner space IS2 into multiple compartments. The second partition may include at least one partition dividing the second inner space IS2 from top to bottom.

As in this embodiment, the second inner space IS2 may be divided from top to bottom by a 1st second partition 331, a 2nd second partition 332, and a 3rd second partition 333.

Figure 3:
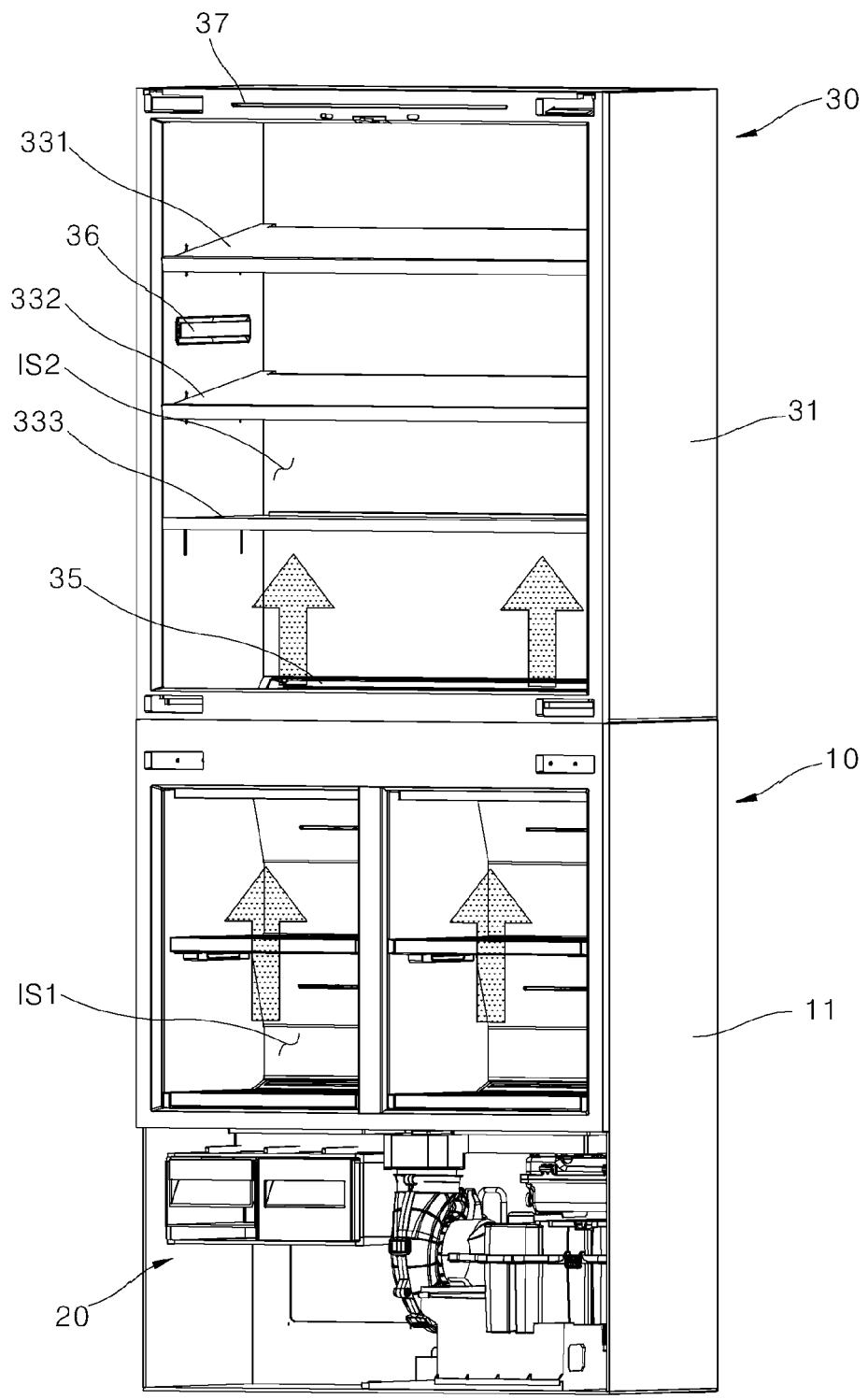
FIG. 3 is a perspective view of the shoe management apparatus according to an embodiment of the present disclosure shown in FIG. 1, with the doors and an electric compartment front panel removed therefrom.

FIG. 3 is a perspective view of the shoe management apparatus 1 according to an embodiment of the present disclosure shown in FIG. 1, with the doors 121, 122, 321, 322 and the electric compartment front panel 201 removed therefrom. In FIG. 3, arrows indicate air flow directions.

As described above, the electric compartment 20 is disposed at a lower portion of the first management apparatus 10. The electric compartment 20 may be formed separately from the first management apparatus 10 or may be formed integrally with the first management apparatus 10. Herein, the present disclosure will be described with reference to an example in which the electric compartment 20 is formed integrally with the first management apparatus 10.

The electric compartment 20 may force a fluid to flow in or out of the electric compartment 20. That is, the electric compartment 20 may supply the fluid to the first inner space IS1 and/or the second inner space IS2. Alternatively, the electric compartment 20 may draw in the fluid from the first inner space IS1 and/or the second inner space IS2. Here, the fluid may be air, steam, or a material containing substances necessary for management of shoes.

The electric compartment 20 may include a main fan 21 and draws in air, dehumidifies the drawn-in air, and discharges the dehumidified air.

The air discharged from the electric compartment 20 may be delivered to the first inner space IS1 of the first management apparatus 10 and/or the second inner space IS2 of the second management apparatus 30. To this end, the shoe management apparatus may be formed with a first fluid path communicating between the main fan 21 in the electric compartment 20 and the first inner space IS1 and a second fluid path communicating between the main fan 21 in the electric compartment 20 and the second inner space IS2.

The air inside the first inner space IS1 may be drawn back into the electric compartment 20. To this end, the shoe management apparatus 1 may be formed with a return fluid path extending through the first inner space IS1 and the electric compartment 20.

The second management apparatus 30 may include a second exhaust port 35 through which the air delivered from the electric compartment 20 is discharged to the second inner space IS2. The second exhaust port 35 may be disposed at a rear bottom of the second inner space IS2 defined by the second cabinet 31, but the second exhaust port 35 may be disposed on any portion of a bottom surface of the second inner space IS2.

In addition, the second management apparatus 30 may include a circulation filter 36 removing harmful substances from the air inside the second inner space IS2. The circulation filter 36 may be disposed on an inner side surface of the second cabinet 31. Although one circulation filter 36 is shown in FIG. 3, it will be understood that the present disclosure is not limited thereto and the second management apparatus 30 may include multiple circulation filters 36. For example, another circulation filter may be disposed at a side opposite the circulation filter 36 shown in FIG. 3.

In addition, the second management apparatus 30 may include a front discharge port 37 through which air in the second inner space IS2 is discharged to an outside of the shoe management apparatus 1. The front discharge port 37 may be disposed on an upper front surface of the second cabinet 31 or any outer surface of the second cabinet 31.

In addition, at least one of the partitions 331, 332, 333 of the second management apparatus 30 may be variable in angle with respect to a front-to-rear direction of the shoe management apparatus. That is, at least one of the partitions 331, 332, 333 of the second management apparatus 30 may be movable so as to be positioned at various different angles. When the multiple partitions are configured to be variable in angle with respect to the front-to-rear direction, each of the multiple partitions may be independently variable in angle with respect to the front-to-rear direction. With the configuration in which at least one of the partitions 331, 332, 333 is variable in angle with respect to the front-to-rear direction, the air in the second inner space IS2 can flow in various forms, thereby securing uniform ventilation throughout the second inner space IS2, including corners thereof.

As shown in FIG. 1, FIG. 2 and FIG. 3, the shoe management apparatus 1 according to an embodiment of the present disclosure may include: the first management apparatus 10 including the electric compartment 20 and formed with the first inner space IS1 for storing shoes; and the second management apparatus 30 disposed on the upper surface of the first management apparatus 10 and formed with the second inner space IS2 for storing shoes. The electric compartment 20 may be disposed at the lower portion of the first management apparatus 10, and the first inner space IS1 may be formed on an upper side of the space for the electric compartment 20. The first management apparatus 10 may perform at least one operation selected from among contaminant removal, sterilization, deodorization, dehumidification, drying, and coating for shoes placed in the first inner space IS1 with relatively high intensity for a relatively short period of time (or any intensity level for any amount of time), and the second management apparatus 30 may perform at least one operation selected from among sterilization, ventilation, and dehumidification of the second inner space IS2 with relatively low intensity for a relatively long period of time (or with any intensity level for any amount of time), the intensity of the at least one operation of the second management apparatus 30 is less than the intensity of the at least one operation of the first management apparatus 10.

Here, "relatively high intensity" means that the temperature of the steam used in the sterilization operation is relatively high, the intensity of the UV rays used in the sterilization operation is relatively high, or the intensity of the airflow applied to shoes is relatively high.

As such, the shoe management apparatus according to this embodiment of the present disclosure can quickly remove contamination of shoes while allowing long-term storage of shoes without deterioration of the shoes. In addition, the shoe management apparatus according to this embodiment of the present disclosure can be built-in in an entrance room of a building due to structural compactness thereof.

In addition, according to this embodiment of the present disclosure, dehumidified air can be supplied to two management apparatuses using one electric compartment. Thus, it is possible to reduce the overall size of the shoe management apparatus.

Figure 4:
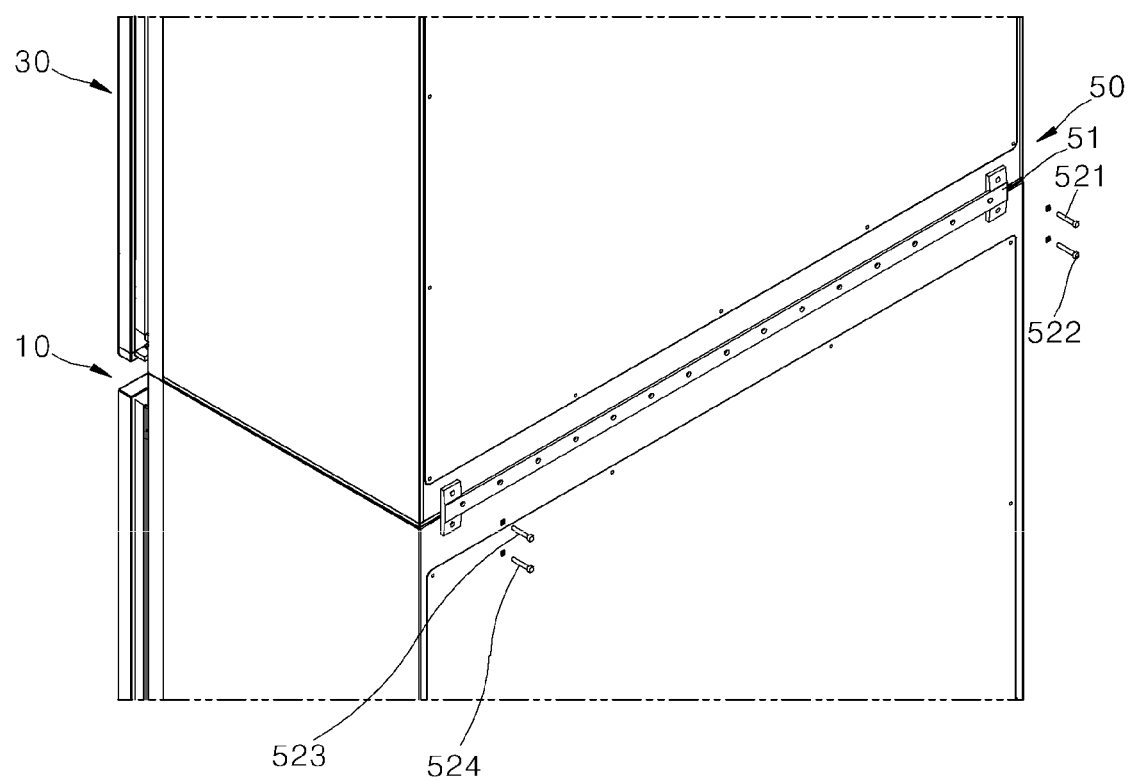
FIG. 4 is a partial view of a back surface of the shoe management apparatus according to an embodiment of the present disclosure shown in FIG. 1.

FIG. 4 is a partial view of a back surface of the shoe management apparatus according to an embodiment of the present disclosure shown in FIG. 1. Referring to FIG. 4, the shoe management apparatus may include a longitudinal fastener 50 coupling the first management apparatus 10 to the second management apparatus 30. The longitudinal fastener 50 may include a longitudinal connection bar 51 and multiple longitudinal connection screws 521, 522, 523, 524.

Referring to FIG. 4, the shoe management apparatus according to an embodiment of the present disclosure may have a structure in which the first management apparatus 10 and the second management apparatus 30 are stacked vertically (i.e., in a vertical direction).

The longitudinal fastener 50 may couple the stacked first management apparatus 10 and second management apparatus 30 to each other. The longitudinal fastener 50 may be disposed on the back surface (i.e., rear surface) of the shoe management apparatus 1.

The longitudinal connection bar 51 may be disposed at a joint between the first management apparatus 10 and the second management apparatus 30 to be partially located on a back surface of the first management apparatus 10 and partially located on a back surface (i.e., rear surface) of the second management apparatus 30. The longitudinal connection bar 51 may have a horizontally elongated "H" shape, as viewed from behind the shoe management apparatus.

The longitudinal connection screws 521, 522, 523, 524 serve to securely couple the connection bar 51 to the first management apparatus 10 or the second management apparatus 30. Specifically, the longitudinal connection screws 521, 523 may couple the longitudinal connection bar 51 to the second management apparatus 30, and the longitudinal connection screws 522, 524 may couple the longitudinal connection bar 51 to the first management apparatus 10. When viewed from behind the shoe management apparatus, the longitudinal connection screws 521, 522 may be disposed on the right and the connection screws 523, 524 may be disposed on the left.

Figure 5:
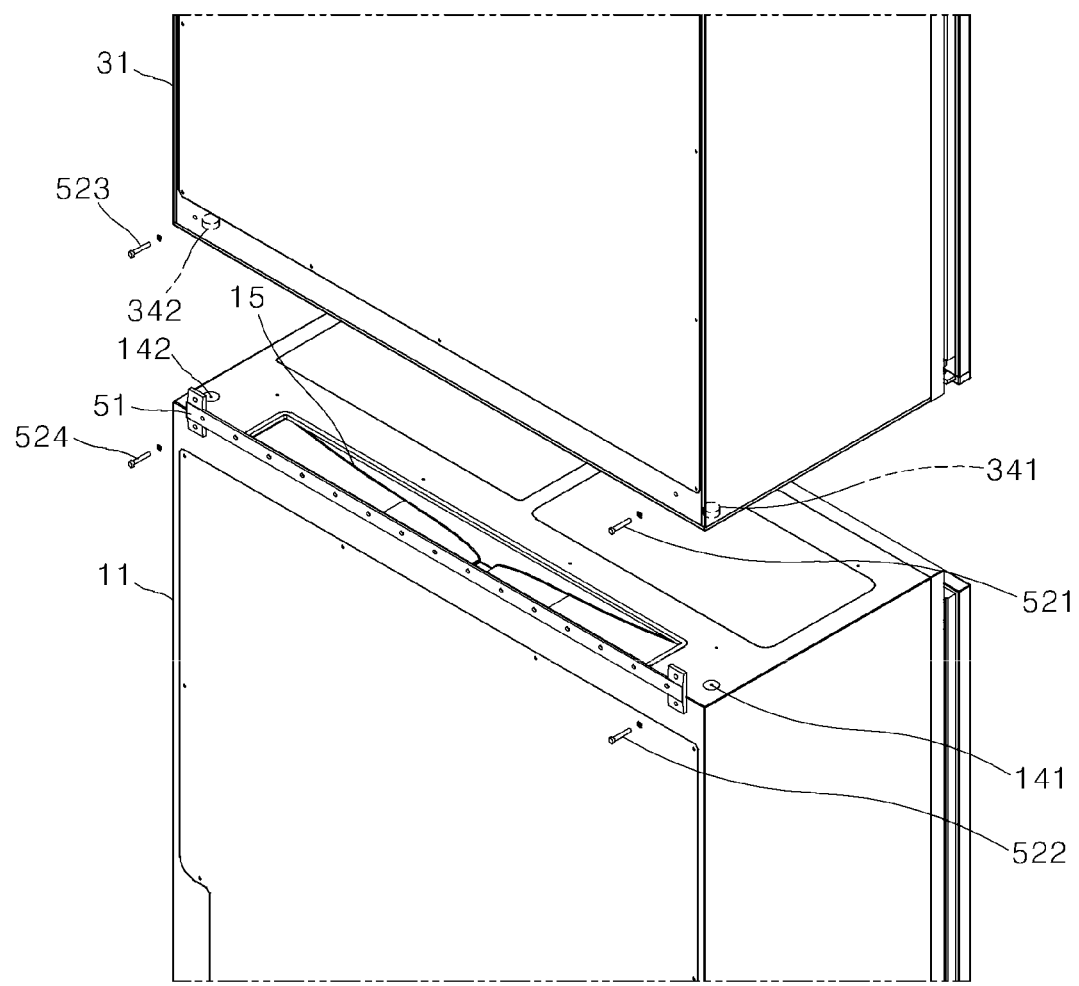
FIG. 5 is a partial view of the shoe management apparatus according to an embodiment of the present disclosure shown in FIG. 1, with a first management apparatus separated from a second management apparatus.

FIG. 5 is a partial view of the shoe management apparatus 1 according to an embodiment of the present disclosure shown in FIG. 1, with the first management apparatus 10 separated from the second management apparatus 30.

The first cabinet 11 of the first management apparatus 10 may include first signal contacts 141, 142 disposed on an upper surface thereof. In addition, the second cabinet 31 of the second management apparatus 30 may include second signal contacts 341, 342 disposed on a lower surface thereof.

Upon stacking the second management apparatus 30 on the upper surface of the first management apparatus 10, the first signal contacts 141, 142 may contact the second signal contacts 341, 342, respectively. The first management apparatus 10 may exchange necessary signals (i.e., data) with the second management apparatus 30 through signal transmission via the first signal contacts 141, 142 and the second signal contacts 341, 342. The signal transmission may be a wireless transmission, such as Bluetooth™, Zigbee™, Wi-Fi, etc.

In addition, the first management apparatus 10 may include a first exhaust port 15 disposed at an upper end thereof (i.e., the upper surface). Upon stacking the second management apparatus 30 on the upper surface of the first management apparatus 10, the first exhaust port 15 may be connected to the second exhaust port 35 of the second management apparatus 30. In this way, the air delivered from the electric compartment 20 can be discharged into the second inner space IS2 sequentially through the first exhaust port 15 of the first management apparatus 10, and through the second exhaust port 35 of the second management apparatus 30.

Figure 6:
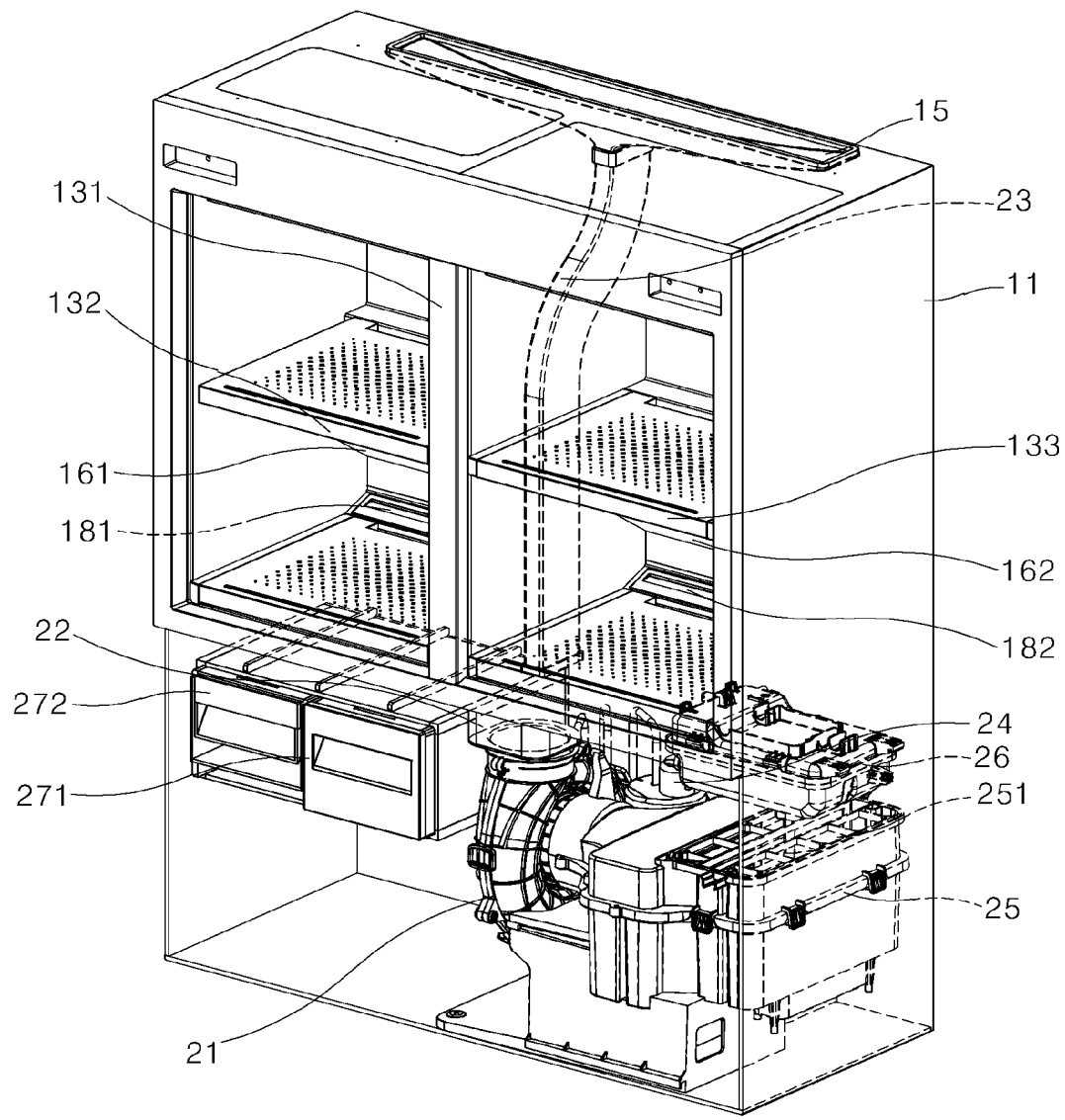
FIGS. 6, 7 and 8 are views illustrating the configuration of the first management apparatus of the shoe management apparatus according to an embodiment of the present disclosure.
Figure 7:
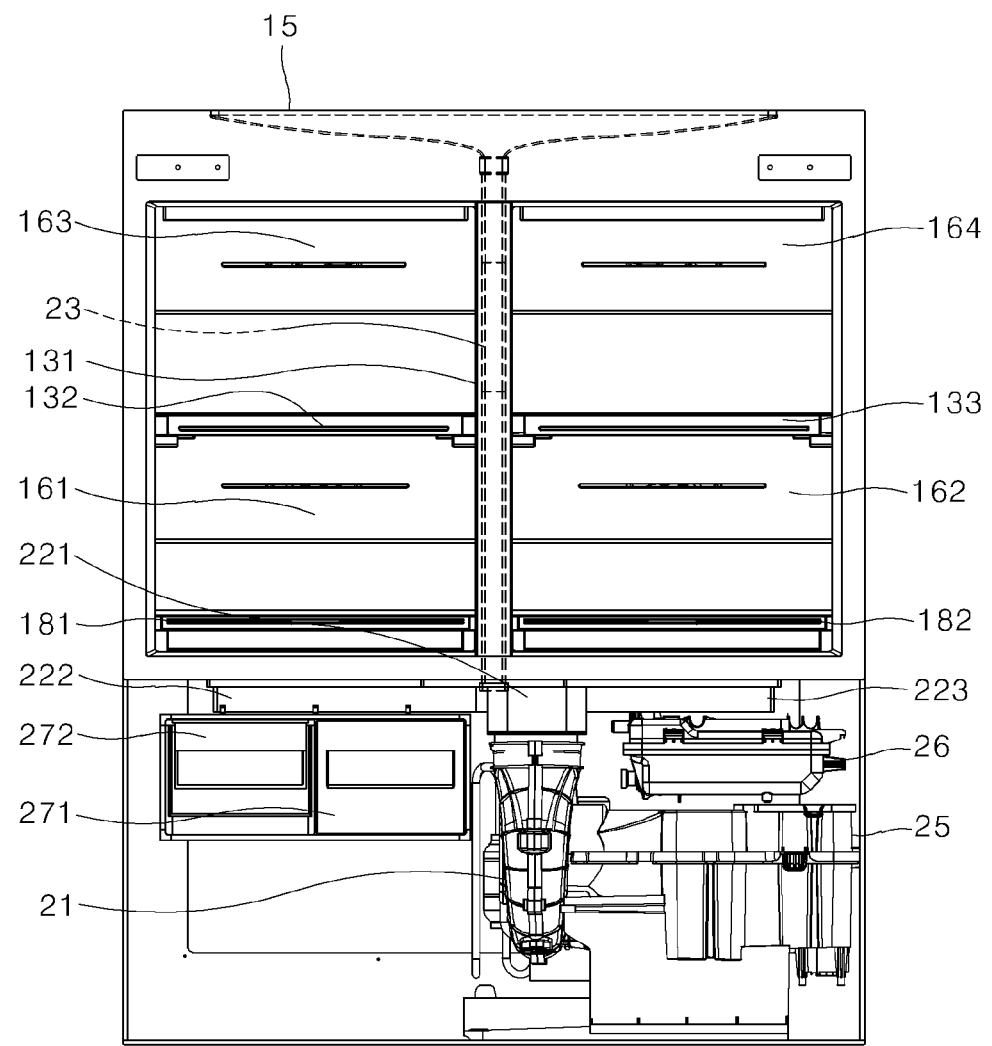
Figure 8:
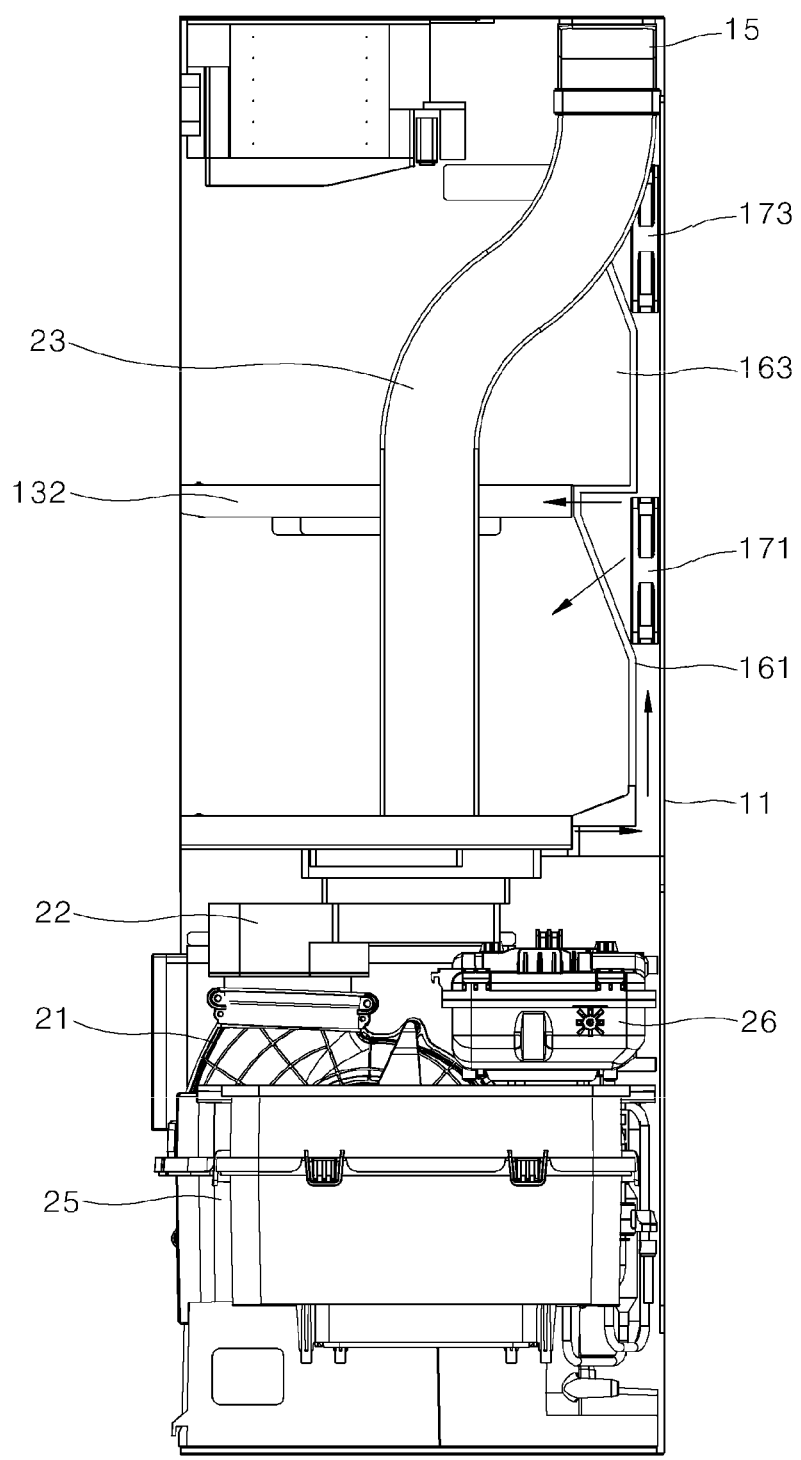

FIG. 6, FIG. 7 and FIG. 8 are views illustrating the configuration of the first management apparatus 10 of the shoe management apparatus 1 according to an embodiment of the present disclosure. FIG. 6 is a perspective view of the first management apparatus 10, FIG. 7 is a front view of the first management apparatus 10, and FIG. 8 is a side sectional view of the first management apparatus 10. In FIG. 6, FIG. 7 and FIG. 8, the first management apparatus 10 is partially transparent to allow an inside thereof to be viewed.

As described above, the first management apparatus 10 may include: a first cabinet 11 defining a first inner space (IS1 of FIG. 3) for storing shoes and a space for an electric compartment (20 of FIG. 3); and a first exhaust port 15 disposed at a rear upper end of the first cabinet 11 to discharge air therethrough.

Referring to FIG. 6, the first inner space IS1 may be divided by a 1st first partition 131, a 2nd first partition 132, and a 3rd first partition 133. The 1st first partition 131 may be provided in the form of a vertically extending panel to divide the first inner space IS1 from side to side. The 2nd first partition 132 may be provided in the form of a horizontally extending panel to divide a left compartment partitioned off by the 1st first partition 131 from top to bottom. The 3rd first partition 133 may be provided in the form of a horizontally extending panel to divide a right compartment partitioned off by the 1st first partition 131 from top to bottom.

Referring to FIG. 7, the compartments of the first inner space IS1 partitioned off by the 1st first partition 131, the 2nd first partition 132, and the 3rd first partition 133 may be provided therein with first inner panels 161, 162, 163, 164, respectively.

In addition, the first inner space IS1 may be provided at a rear lower edge thereof with steam exhaust ports 181, 182. The steam exhaust ports 181, 182 allow steam generated by a steam generator 26 to be discharged therethrough. To this end, the first management apparatus may include a fluid duct directly connecting the steam generator 26 to each of the steam exhaust ports 181, 182. Alternatively, the steam generated by the steam generator 26 may be discharged into the housing 25 and then forced to flow to the steam exhaust ports 181, 182 through the main fan 21 and an air distributor 221, 222, 223.

Referring to FIG. 8, the first inner panels 161, 162, 163, 164 may be disposed at rear upper portions of the compartments of the first inner space IS1 partitioned off by the 1st first partition 131, the 2nd first partition 132, and the 3rd first partition 133, respectively (the rear is shown to the right in FIG. 8). In addition, each of the first inner panels 161, 162, 163, 164 may be disposed to be inclined with respect to an inner surface of the first cabinet 11 such that an upper end thereof is located ahead of a lower end thereof. That is, each of the first inner panels 161, 162, 163, 164 may define a space for accommodating a first blower fan 171 or a second blower fan 173 and an air flow path in a region over toe caps of shoes placed in the first inner space IS1. The first blower fans 171 may be disposed on a rear surface of the first cabinet 11 behind the first inner panel 161 and/or the second inner panel 162. The second blower fans 173 may be disposed on a rear surface of the first cabinet 11 behind the third inner panel 163 and/or the fourth inner panel 164.

Air discharged from the main fan 21 may be forced to flow into a space between the inner surface of the first cabinet 11 and each of the first inner panels 161, 162, 163, 164 before being discharged into the first inner space IS1 by the first blower fans 171.

That is, according to this embodiment of the present disclosure, with the blower fans disposed in the region over the toe caps of shoes, which would otherwise be an idle space, the shoe management apparatus can increase the flow rate of air therein.

Referring back to FIG. 6, the electric compartment (20 of FIG. 3) may include a main fan 21, an air distributor 22, a longitudinal connection pipe 23, a heat pump 24, a housing 25, a steam generator 26, a water supply container 271, and a drain container 272. The water supply container 271 and the drain container 272 may be disposed at one lateral side of the main fan 21 (for example, at the left of the main fan 21, as viewed from the front), the heat pump 24, the housing 25, and the steam generator 26 may be disposed at the other lateral side of the main fan 21 (for example, at the right of the main fan 21, as viewed from the front), and the air distributor 22 and the longitudinal connection pipe 23 may be disposed above the main fan 21.

The main fan 21 draws in air from the housing 25 by creating a vacuum and discharges the drawn-in air.

The air distributor 22 may distribute the air discharged from the main fan 21 to the first exhaust port 15 and/or the first inner space IS1 defined by the first cabinet 11.

Referring to FIG. 7, the air distributor 22 may include a central connection portion 221, a first arm 222, and a second arm 223.

The central connection portion 221 is connected to the main fan 21 to distribute the air delivered from the main fan 21 in multiple directions (for example, in three directions). In some embodiments, the central connection portion 221 may guide the air delivered from the main fan 21 in a specific direction selected from the multiple directions.

The first arm 222 and the second arm 223 may be connected to opposite lateral sides of the central connection portion 221, respectively, to guide the air delivered from the central connection portion 221 to the first inner space IS1 defined by the first cabinet 11.

Referring back to FIG. 6, the longitudinal connection pipe 23 may vertically extend through an inside of the 1st first partition 131. The longitudinal connection pipe 23 may guide the air delivered from the main fan 21 to the first exhaust port 15. The longitudinal connection pipe 23 may connect the air distributor 22 (more specifically, the central connection portion 221) to the first exhaust port 15.

The heat pump 24 serves to heat and condense air. The heat pump 24 may include a condenser condensing and removing moisture in air and an evaporator heating air. The condenser and/or the evaporator may be disposed inside the housing 25.

The housing 25 may define a space for drying and/or heating air. The housing 25 may be formed on an upper surface thereof with an opening 251 through which air is introduced into the housing, may be formed therein with a space for accommodating the heat pump (more specifically, the condenser and/or the evaporator of the heat pump), and may be formed on a side surface thereof with an opening connected to the main fan 21 (specifically, a housing of the main fan). In addition, the housing 25 may define a space for accommodating the heat pump (more specifically, the condenser and/or the evaporator of the heat pump). Although not shown, the first management apparatus may further include a fluid path communicating between the opening 251 formed on the upper surface of the housing 25 and the first inner space IS1 defined by the first cabinet 11 and/or the second inner space IS2 defined by the second cabinet 31.

The steam generator 26 generates steam by heating water. The steam generator 26 may heat water to 100° C. The steam generator 26 may receive water from the water supply container 271.

The water supply container 271 may be detachably coupled to the first cabinet 11. The water supply container 271 may supply water to the steam generator 26.

The drain container 272 may be detachably coupled to the first cabinet 11. The drainage container 272 may collect water condensed by the heat pump 24 (more specifically, the condenser) inside the housing 25.

Figure 9:
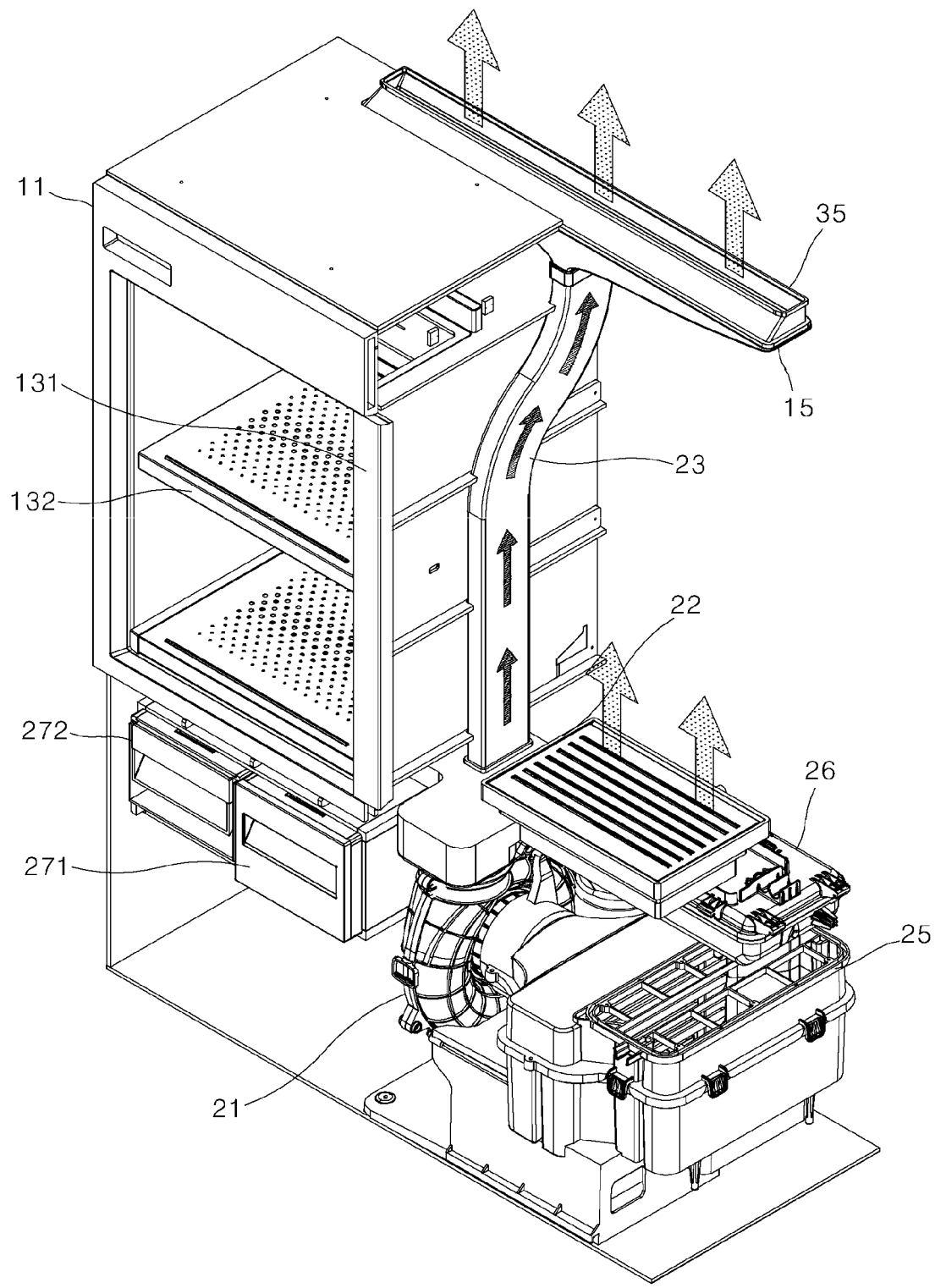
FIG. 9 is a view illustrating an airflow discharged from an electric compartment of the first management apparatus of the shoe management apparatus according to an embodiment of the present disclosure.

FIG. 9 is a view illustrating the flow of air discharged from the electric compartment 20 of the first management apparatus 10 of the shoe management apparatus according to an embodiment of the present disclosure.

Air introduced into the housing 25 is dried and/or heated before being drawn into the main fan 21. The air discharged from the main fan 21 may be supplied to the first inner space IS1 defined by the first cabinet 11 through the air distributor 22. Alternatively, the air discharged from the main fan 21 may be delivered to the first exhaust port 15 through the air distributor and the longitudinal connection pipe 23. The air delivered to the first exhaust port 15 may be supplied to the second inner space IS2 defined by the second cabinet 31 through the second exhaust port 35 of the second management apparatus 30. Alternatively, the air discharged from the main fan 21 may be supplied to both the first inner space IS1 and the second inner space IS2 in the same manner as described above.

Figure 10:
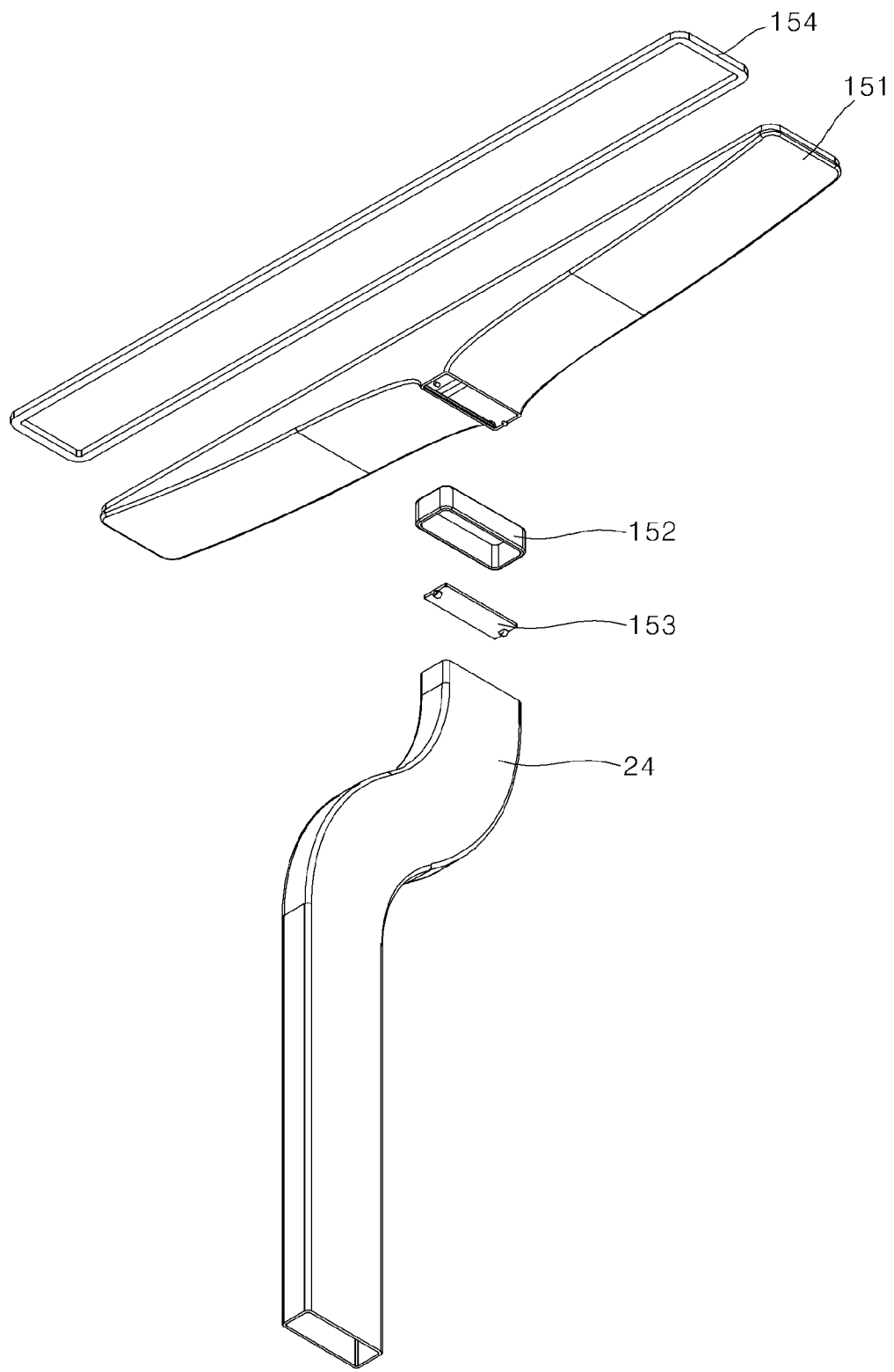
FIG. 10 is a view illustrating the configuration of a first exhaust port of the first management apparatus of the shoe management apparatus according to an embodiment of the present disclosure.

FIG. 10 is an exploded perspective view of the first exhaust port 15 of the first management apparatus 10 of the shoe management apparatus 1 according to an embodiment of the present disclosure. Referring to FIG. 10, the first exhaust port 15 may include a diffuser 151, a first exhaust port lower packing 152, a control damper 153, and a first exhaust port upper packing 154.

The diffuser 151 may have a smaller cross-sectional area at an air inlet point thereof and a larger cross-sectional area at an air outlet point to diffuse air discharged therethrough. The diffuser 151 may be disposed at the rear upper end of the first cabinet 11 of the first management apparatus 10.

The first exhaust port lower packing 152 may be disposed between the longitudinal connection pipe 23 and the diffuser 151. The first exhaust port lower packing 152 may be formed of an elastic material such as rubber. The first exhaust port lower packing 152 prevents air leakage through a gap between the longitudinal connection pipe 23 and the diffuser 151.

The control damper 153 may be disposed at the air inlet point of the diffuser 151. For example, the control damper 153 may be disposed at a joint between the diffuser 151 and the longitudinal connection pipe 23. The control damper 153 serves to adjust the flow rate of air discharged through the diffuser 151. That is, the control damper 153 may be operable to selectively supply air to the second inner space IS2.

The first exhaust port upper packing 154 may be disposed between the diffuser 151 and a first top opening formed on the upper surface of the first cabinet 11, the first top opening being configured to dispose the first exhaust port 15 therein. The first exhaust port lower packing 154 may be formed of an elastic material such as rubber. The first exhaust port upper packing 154 prevents air leakage through a gap between the first cabinet 11 and the diffuser 151. In addition, the first exhaust port upper packing 154 may also serve to maintain airtightness between the first exhaust port 15 (more specifically, the diffuser 151) and the second exhaust port 35 (more specifically, a second inlet 352) with the second management apparatus 30 disposed on the upper surface of the first management apparatus 10.

Figure 11:
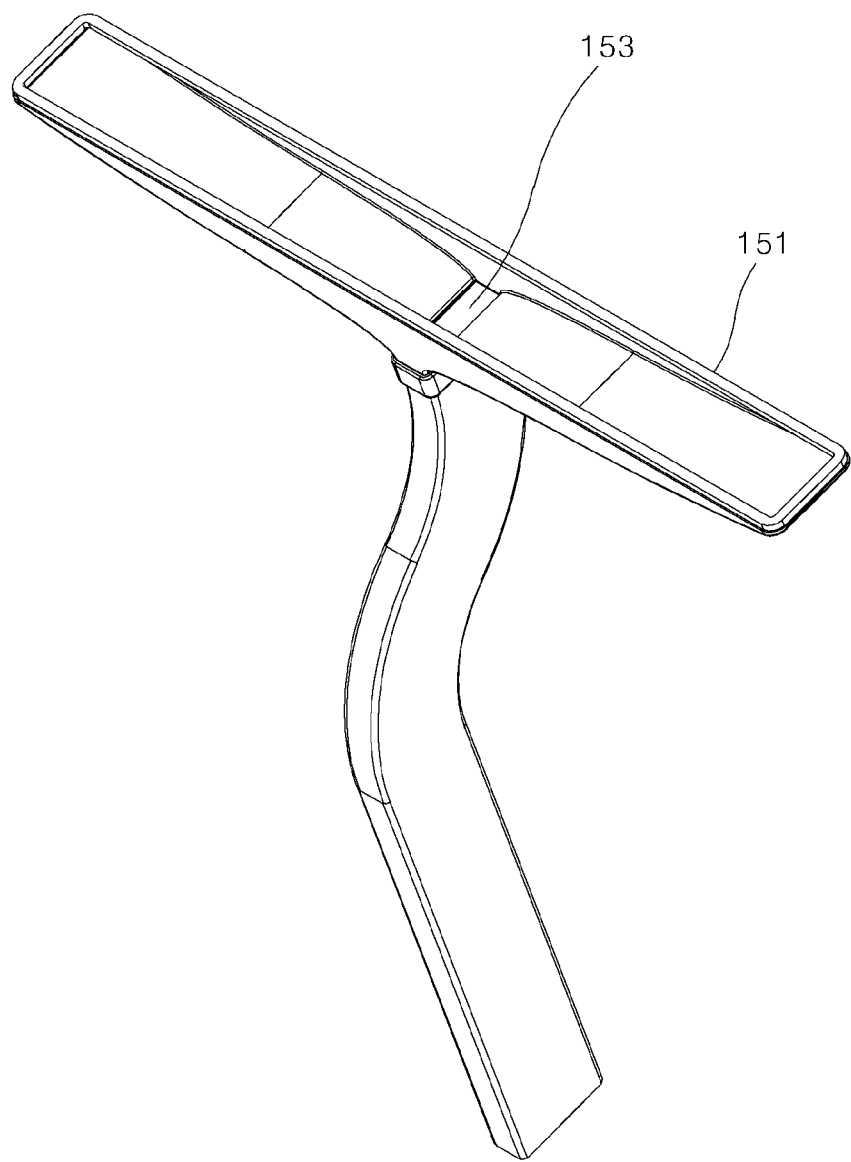
FIG. 11 and FIG. 12 are views illustrating operations of a damper of the first exhaust port of the first management apparatus of the shoe management apparatus according to an embodiment of the present disclosure.
Figure 12:
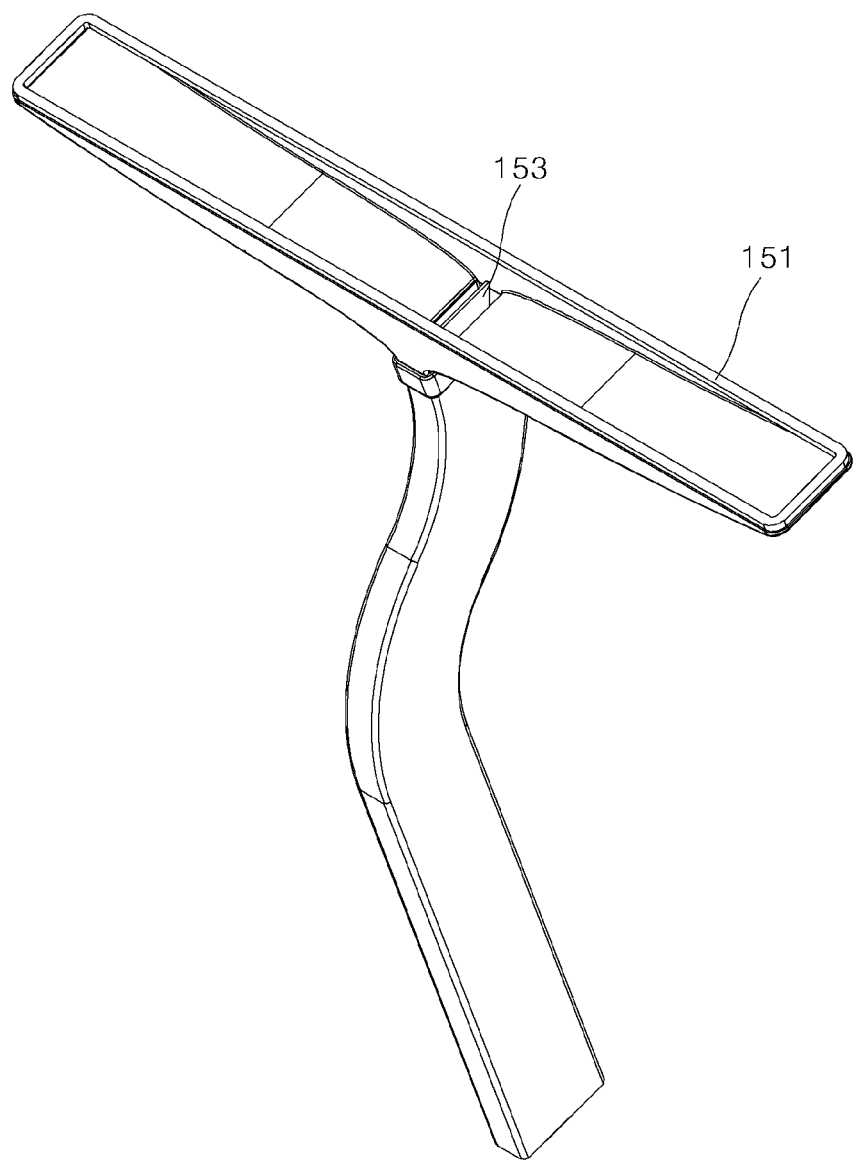

FIG. 11 and FIG. 12 are views illustrating an operation of the damper 153 of the first exhaust port 15 of the first management apparatus 10 of the shoe management apparatus 1 according to an embodiment of the present disclosure. FIG. 11 is a view of the first exhaust port, wherein the damper 153 is in a closed position, and FIG. 12 is a view of the first exhaust port, wherein the damper 153 is in an open position.

When the damper 153 is in the closed position, as shown in FIG. 11, air discharged from the electric compartment 20 is not allowed to be discharged through the first exhaust port 15, causing no air flow (circulation) in the second inner space IS2 of the second management apparatus 30.

When the damper 153 is in the open position, as shown in FIG. 2, air delivered from the electric compartment 20 is allowed to be diffusely discharged through the first exhaust port 15, causing an air flow in the second inner space IS2 of the second management apparatus 30.

Figure 13:
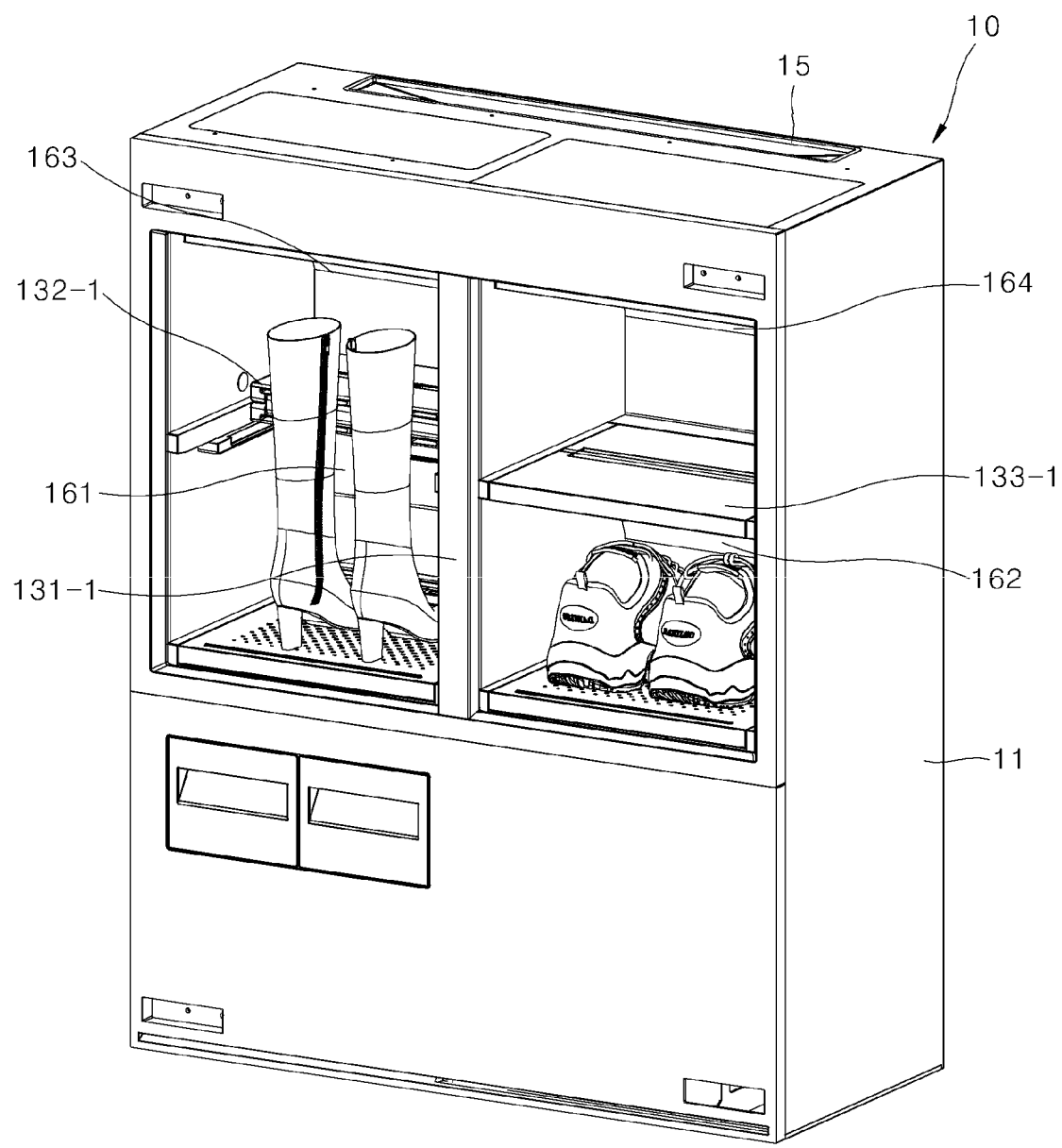
FIG. 13 is a perspective view of the first management apparatus of the shoe management apparatus according to an embodiment of the present disclosure shown in FIG. 1, with the doors removed therefrom.

FIG. 13 is a perspective view of the first management apparatus 10 of the shoe management apparatus 1 according to an embodiment of the present disclosure shown in FIG. 1, with the doors 121, 122 removed therefrom.

The first management apparatus 10 may include multiple partitions 131-1, 132-1, 133-1 and multiple inner panels 161, 162, 163, 164. The first management apparatus 10 may further include multiple blower fans disposed at the rear of the multiple inner panels 161, 162, 163, 164, respectively.

In terms of arrangement and function, the 1st first partition 131-1, the 2nd first partition 132-1, and the 3rd first partition 133-1 may be substantially the same as the 1st first partition 131, the 2nd first partition 132, and the 3rd first partition 133 described above with reference to FIG. 2, respectively.

However, according to this embodiment, the 2nd first partition 132-1 and/or the 3rd first partition 133-1 may be variable in length with reference to the front-to-rear direction. For example, as shown in FIG. 13, the 2nd first partition 132-1 and/or the 3rd first partition 133-1 may be folded such that one portion of the partition 132-1 and/or the partition 133-1 lies on an upper surface of the other portion thereof to have a relatively short length with reference to the front-to-rear direction. Alternatively, the 2nd first partition 132-1 and/or the 3rd first partition 133-1 may be unfolded to have a relatively long length with reference to the front-to-rear direction.

In addition, according to this embodiment, the 2nd first partition 132-1 and/or the 3rd first partition 133-1 may be variable in direction and location where air is discharged therethrough. For example, the 2nd first partition 132-1 and/or the 3rd first partition 133-1 may be switched between a position in which air is discharged therethrough in a downward direction from a front region of the first inner space IS1 of the first management apparatus 10 with reference to the front-rear direction and a position in which air is discharged therethrough in a forward direction from a middle region of the first inner space IS1 of the first management apparatus 10 with reference to the front-to-rear direction.

Herein, the front region of the first inner space IS1 with reference to the front-rear direction refers to a front section among three sections formed by virtually dividing the first inner space IS1 from front to rear. In addition, the middle region of the first inner space IS1 with reference to the front-rear direction refers to a middle section among the three sections formed by virtually dividing the first inner space IS1 from front to rear. Further, a rear region of the first inner space IS1 with reference to the front-rear direction refers to a rear section among the three sections formed by virtually dividing the first inner space IS1 from front to rear.

The multiple inner panels 161, 162, 163, 164 may be disposed at rear upper portions of the compartments partitioned off by the partitions 131-1, 132-1, 133-1, respectively. In addition, an air flow path and a space for accommodating the blower fan may be defined between the first cabinet 11 and each of the multiple inner panels 161, 162, 163, 164. Further, each of the multiple inner panels 161, 162, 163, 164 may be disposed at an acute angle to the inner surface of the first cabinet 11. That is, each of the multiple inner panels 161, 162, 163, 164 may be disposed with an upper end thereof located ahead of a lower end thereof.

In addition, each of the multiple inner panels 161, 162, 163, 164 may be formed with an inner panel exhaust port. That is, each of the multiple inner panels 161, 162, 163, 164 allows air to be discharged therethrough in an obliquely downward direction from the rear of the first inner space IS1 (more specifically, the rear region of each corresponding compartment) with reference to the front-rear direction. The air exhaust direction may be adjusted by changing a relative position of the inner panel exhaust port with respect to the blower fan at the rear of each of the inner panels 161, 162, 163, 164.

Figure 14:
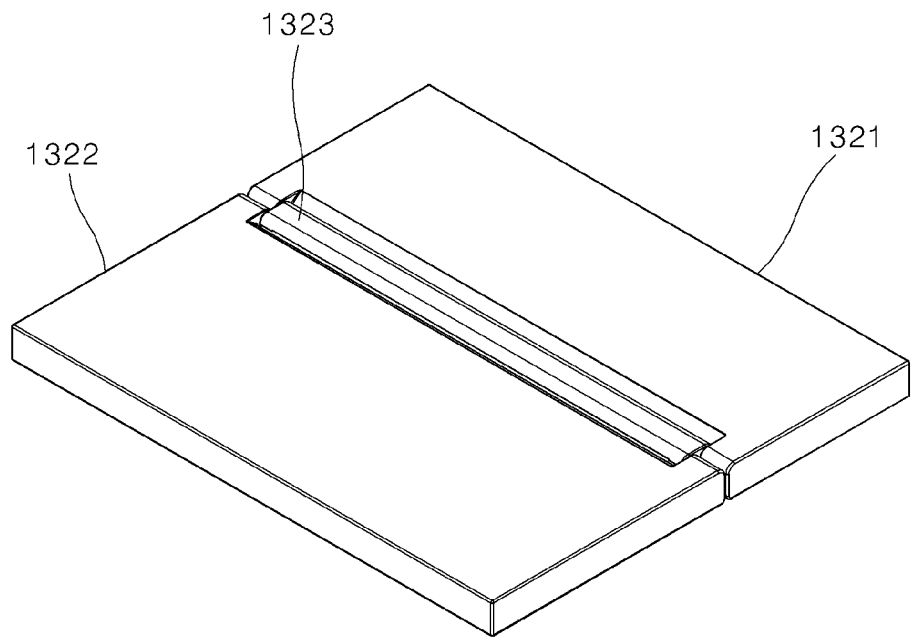
FIG. 14 is a perspective view of a 2nd first partition of the shoe management apparatus according to an embodiment of the present disclosure, wherein the 2nd first partition is in an unfolded position.

FIG. 14 is a perspective view of the 2nd first partition 132-1 of the shoe management apparatus according to an embodiment of the present disclosure, wherein the 2nd first partition 132-1 is in an unfolded position. Referring to FIG. 14, the 2nd first partition 132-1 may include a first plate 1321, a second plate 1322, and a plate connection portion 1323.

The first plate 1321 may be secured to the first cabinet (11 of FIG. 13). More specifically, the first plate 1321 may be secured to the first cabinet (11 of FIG. 13) at a rear portion of the first inner space IS1 defined by the first cabinet (11 of FIG. 13).

The second plate 1322 may be connected to the first plate 1321 through the plate connection portion 1323. When the 2nd first partition is in the unfolded position, the second plate 1322 may be located in front of the first plate 1321.

The plate connection portion 1323 may be pivotally coupled to each of the first plate 1321 and the second plate 1322.

Figure 15:
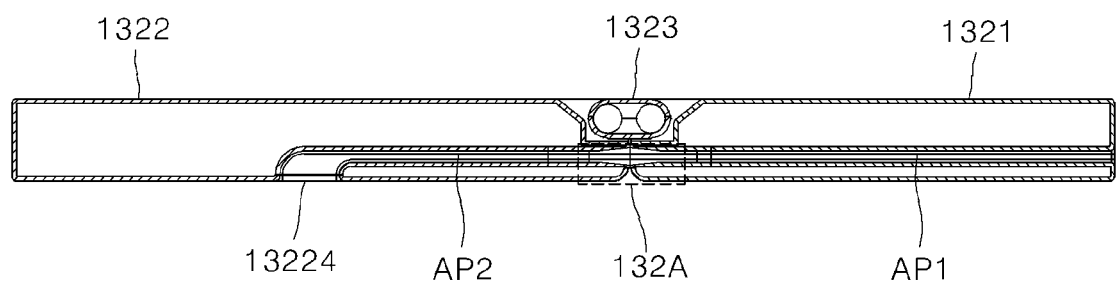
FIG. 15 is a sectional view of a 2nd first partition of the shoe management apparatus according to an embodiment of the present disclosure, wherein the 2nd first partition is in the unfolded position.
Figure 16:
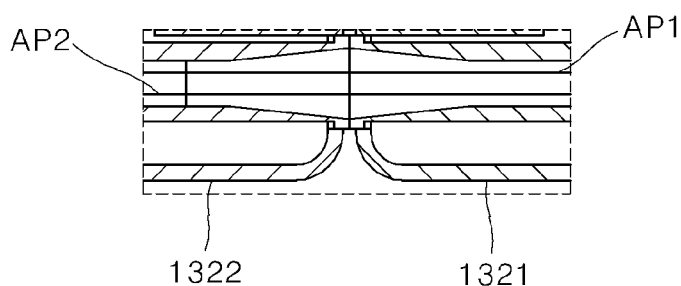
FIG. 16 is an enlarged view of section 132A of FIG. 15.

FIG. 15 is a sectional view of the 2nd first partition 132-1 of the shoe management apparatus according to an embodiment of the present disclosure, wherein the 2nd first partition 132-1 is in the unfolded position. FIG. 16 is an enlarged view of section 132A of FIG. 15.

The first plate 1321 may be formed therein with a first plate fluid path AP1, and the second plate 1322 may be formed therein with a second plate fluid path AP2. In addition, the second plate 1322 may be formed on a lower surface thereof with a second plate exhaust port 13224 through which air is discharged, the second plate exhaust port 13224 may be provided in plurality and may extend longitudinally across the second plate 1322.

The plate connection portion 1323 may be pivotally connected to both a front upper portion of the first plate 1321 and a rear upper portion of the second plate 1322. Accordingly, the front upper portion of the first plate 1321 is secured to the rear upper portion of the second plate 1322 through the plate connection portion 1323. In this state, a rear lower portion of the second plate 1322 is supported by a front lower portion of the first plate 1321, whereby an upper surface of the second plate 1322 and an upper surface of the first plate 1321 can remain connected to each other to form a continuous plane.

When the 2nd first partition 132-1 is in the unfolded position, the first plate fluid path AP1 formed in the first plate 1321 may be connected to the second plate fluid path AP2 formed in the second plate 1322. Accordingly, when the 2nd first partition 132-1 is in the unfolded position, air discharged from the electric compartment (20 of FIG. 3) can be delivered to the second plate exhaust port 13224 through the first plate fluid path AP1 and the second plate fluid path AP2. That is, when the 2nd first partition 132-1 is in the unfolded position, air can be discharged in a downward direction from the front region of the first inner space IP1 through the 2nd first partition 132-1.

Each of the first plate fluid path AP1 and the second plate fluid path AP2 has a larger cross-sectional area at a point at which the first plate fluid path AP1 and the second plate fluid path AP2 meet each other when the 2nd first partition 132-1 is in the unfolded position than at the other points. That is, the first plate fluid path AP1 has the largest cross-sectional area at a front end thereof and the second plate fluid path AP2 has the largest cross-sectional area at a rear end thereof. With this structure, it is possible to provide a smooth flow of air from the first plate fluid path AP1 to the second plate fluid path AP2 when the 2nd first partition 132-1 is in the unfolded position.

Figure 17:
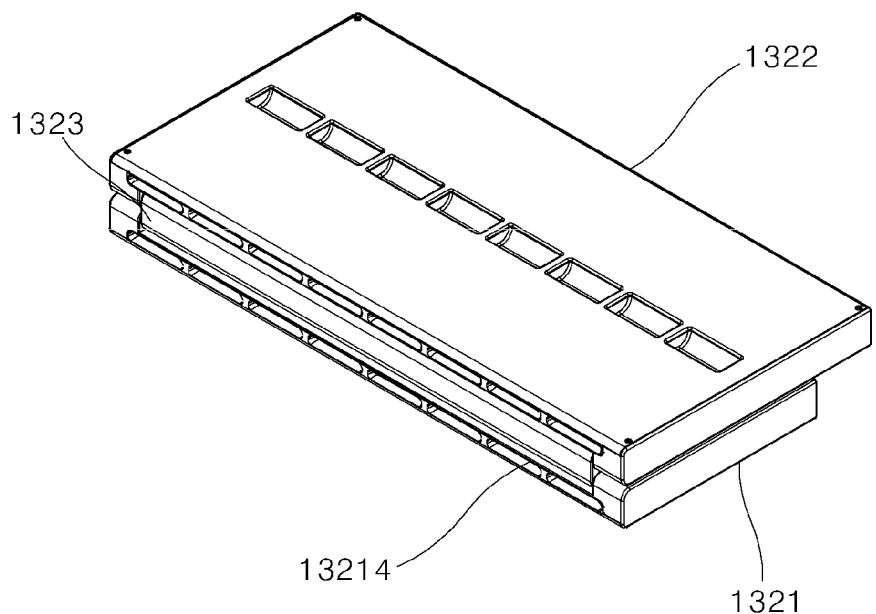
FIG. 17 is a perspective view of the 2nd first partition of the shoe management apparatus according to an embodiment of the present disclosure, wherein the 2nd first partition is in a folded position.
Figure 18:
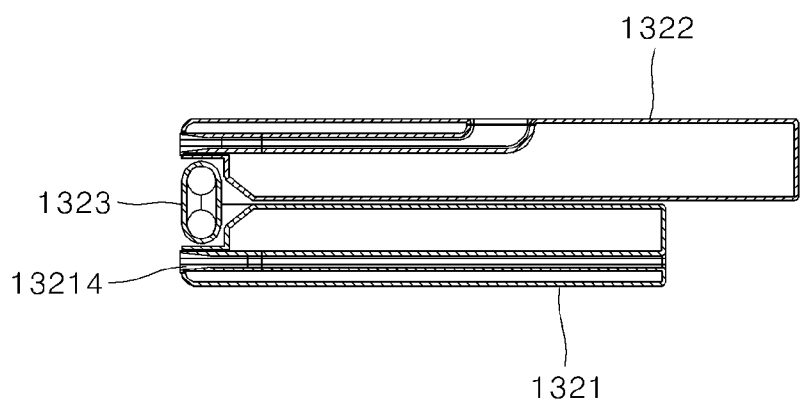
FIG. 18 is a sectional view of the 2nd first partition of the shoe management apparatus according to an embodiment of the present disclosure, wherein the 2nd first partition is in the folded position.

FIG. 17 is a perspective view of the 2nd first partition 132-1 of the shoe management apparatus according to an embodiment of the present disclosure, wherein the 2nd first partition is in a folded position, and FIG. 18 is a sectional view of the 2nd first partition 132-1 of the shoe management apparatus according to an embodiment of the present disclosure, wherein the 2nd first partition is in the folded position.

As described above, the plate connection portion 1323 may be pivotally connected to the front upper portion of the first plate 1321 and the rear upper portion of the second plate 1322. Accordingly, the second plate 1322 may be pivoted upwards about the plate connection portion 1323. When the 2nd first partition 132-1 is in the folded position, the second plate 1322 may be located on the upper surface of the first plate 1321. The first plate 1321 may be formed on a front surface thereof with a first plate exhaust port 13214 through which air is discharged.

When the 2nd first partition 132-1 is in the folded position, air discharged from the electric compartment (20 of FIG. 3) is delivered to the first plate exhaust port 13214 through the first plate fluid path AP1. That is, when the 2nd first partition 132-1 is in the folded position, air can be discharged through the first plate 132-1 in a forward direction from the middle region of the first inner space IS1 with respect to the front-to-rear direction. In addition, as described above, the first plate fluid path AP1 may be increased in cross-sectional area toward the first plate exhaust port 13214. In this way, the air discharged from the first plate exhaust port 13214 can be more widely diffused.

The 3rd first partition 133-1 may have the same structure as the 2nd first partition 132-1 shown in FIGS. 14 to 18.

Figure 19:
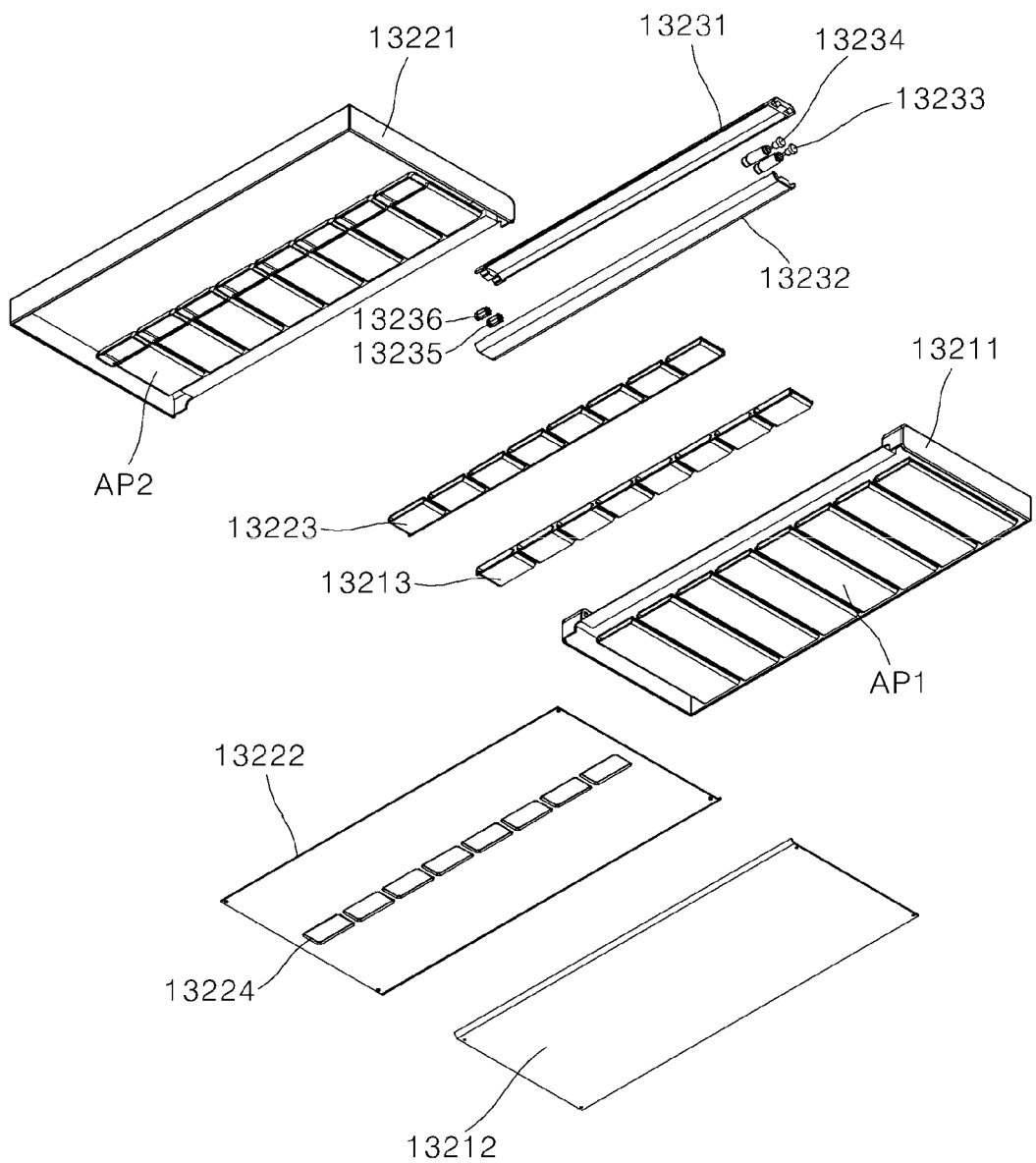
FIG. 19 is an exploded perspective view of the 2nd first partition of the shoe management apparatus according to an embodiment of the present disclosure.

FIG. 19 is an exploded perspective view of the 2nd first partition 132-1 of the shoe management apparatus 1 according to an embodiment of the present disclosure. As described above, the 2nd first partition 132-1 may include the first plate 1321, the second plate 1322, and the plate connection portion 1323. The first plate 1321 may include a first plate upper frame 13211, a first plate lower frame 13212, and a first plate packing 13213. The second plate 1322 may include a second plate upper frame 13221, a second plate lower frame 13222, and a second plate packing 13223. The plate connection portion 1323 may include an upper hinge case 13231, a lower hinge case 13232, hinge motors 13233, 13234, and hinge fasteners 13235, 13236.

The first plate upper frame 13211 may define an exterior of the first plate 1321. The first plate upper frame 13211 may be provided in the form of a cuboid (which may be thin) substantially open at a front and bottom thereof. The first plate fluid path AP1 may be disposed in a space defined by the first plate upper frame 13211. In addition, the first plate upper frame 13211 may be formed at a front upper end thereof with a groove into which the plate connection portion 1323 is partially inserted.

The first plate lower frame 13212 may define a lower exterior of the first plate 1321. The first plate lower frame 13212 may be coupled to the first plate upper frame 13211. The first plate fluid path AP1 may be disposed between the first plate upper frame 13211 and the first plate lower frame 13212.

The first plate packing 13213 may be disposed on front surfaces of the first plate upper frame 13211 and the first plate lower frame 13212 coupled to each other. The first plate packing 13213 may define a front exterior of the first plate 1321. The first plate packing 13213 may define a front end of the first plate fluid path AP1. A front surface of the first plate packing 13213 may define the first plate exhaust port 13214.

The first plate packing 13213 may be formed of an elastic material. For example, the first plate packing 13213 may be formed of rubber. In this way, it is possible to minimize a gap between the first plate fluid path AP1 and the second plate fluid path AP2 when the 2nd first partition 132-1 is in the unfolded position.

The second plate upper frame 13221 may define an exterior of the second plate 1322. The second plate upper frame 13221 may be provided in the form of a thin cuboid open at a rear and bottom thereof. The second plate fluid path AP2 may be disposed in a space defined by the second plate upper frame 13221. In addition, the second plate upper frame 13221 may be formed at a rear upper end thereof with a groove into which the plate connection portion 1323 is partially inserted.

The second plate lower frame 13222 may define a lower exterior of the second plate 1322. The second plate lower frame 13222 may be coupled to the second plate upper frame 13221. The second plate fluid path AP2 may be disposed between the second plate upper frame 13221 and the second plate lower frame 13222.

The second plate packing 13223 may be disposed on back surfaces of the second plate upper frame 13221 and the second plate lower frame 13222 coupled to each other. The second plate packing 13223 may define a rear exterior of the second plate 1322. The second plate packing 13223 may define a rear end of the second plate fluid path AP2.

The second plate packing 13223 may be formed of an elastic material. For example, the second plate packing 13223 may be formed of rubber. In this way, it is possible to minimize a gap between the first plate fluid path AP1 and the second plate fluid path AP2 when the 2nd first partition 132-1 is in the unfolded position.

The upper hinge case 13231 may define an upper exterior of the plate connection portion 1323.

The lower hinge case 13232 may be coupled to a lower surface of the upper hinge case 13231 and may define a lower exterior of the plate connection portion 1323.

The hinge motors 13233, 13234 may be disposed at one lateral side of a space between the upper hinge case 13231 and the lower hinge case 13232 coupled to each other. The hinge motors 13233 and 13234 may provide driving force necessary to fold or unfold the 2nd first partition 132-1.

The hinge fasteners 13235, 13236 may be disposed in the space between the upper hinge case 13231 and the lower hinge case 13232 coupled to each other to be opposite the hinge motors 13233, 13234. Each of the hinge fasteners 13235, 13236 may be pivotally coupled to the upper hinge case 13231 and the lower hinge case 13232 coupled to each other and the first plate 1321 (more specifically, the first plate upper frame 13211) or the second plate 1322 (more specifically, the second plate upper frame 13221).

Figure 20:
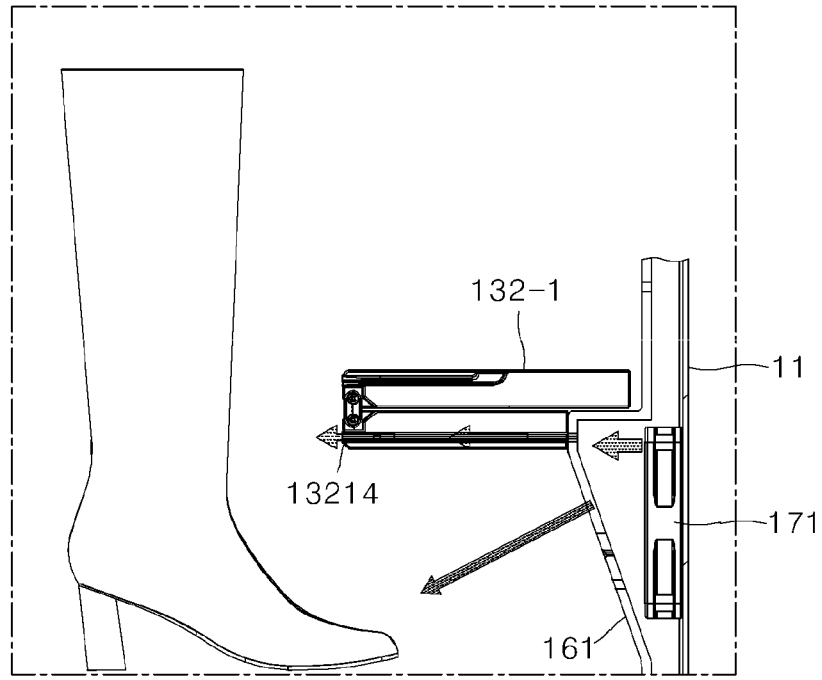
FIG. 20 shows a case in which a boot is placed in the first management apparatus of the shoe management apparatus according to an embodiment of the present disclosure.
Figure 21:
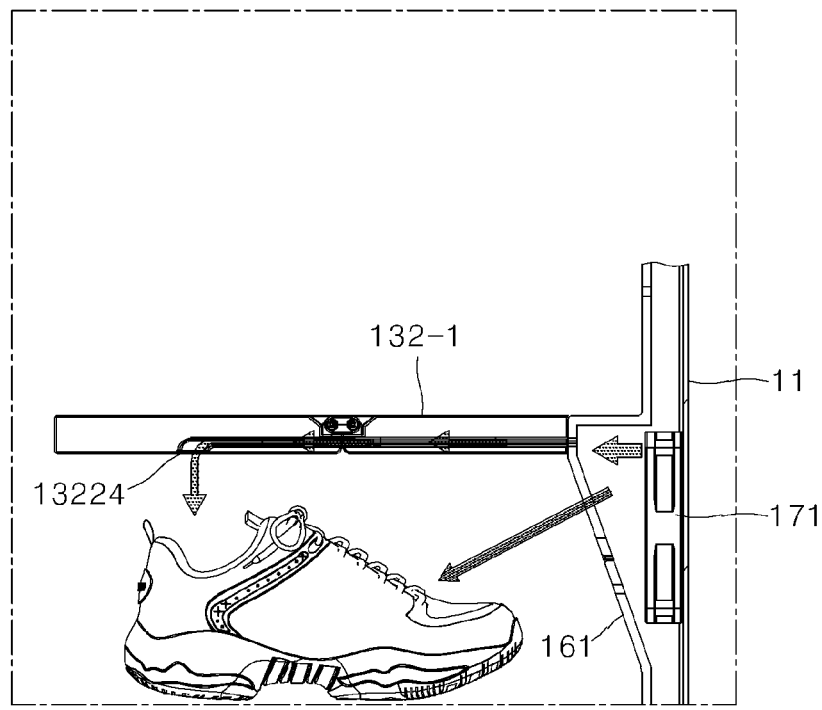
FIG. 21 shows a case in which a sneaker is placed in the first management apparatus of the shoe management apparatus according to an embodiment of the present disclosure.

FIG. 20 shows a case in which a boot is placed in the first management apparatus 10 of the shoe management apparatus 1 according to an embodiment of the present disclosure, and FIG. 21 shows a case in which a sneaker is placed in the first management apparatus 10 of the shoe management apparatus 1 according to an embodiment of the present disclosure.

For the boot placed in the first inner space IS1 of the first management apparatus 10, the 2nd first partition 132-1 is folded such that air can be discharged therethrough in a forward direction from the middle region of the first inner space IS1 with respect to the front-to-rear direction. In this way, it is possible to remove contaminants from a shaft of the boot and, if necessary, to coat the shaft.

For the sneaker placed in the first inner space IS1 of the first management apparatus 10, the 2nd first partition 132-1 is unfolded such that air can be discharged therethrough in a downward direction from the front region of the first inner space IS1. In this way, it is possible to more effectively remove dust, sweat, and the like from inside the sneaker.

In addition, according to an embodiment of the present disclosure, the amount of air discharged through the 2nd first partition 132-1 can be increased due to operation of the first blower fan 171.

Further, the first blower fan 171 and the first inner panel 161 may allow air to flow in an obliquely downward direction from the rear of the first inner space IS1. That is, the first blower fan 171 may force air to be discharged to a toe cap of the boot through the first inner panel 161. Thus, the shoe management apparatus according to an embodiment of the present disclosure can more efficiently perform an operation of removing contaminants from the shaft and toe cap of the boot or coating the shaft and toe cap of the boot.

Figure 22:
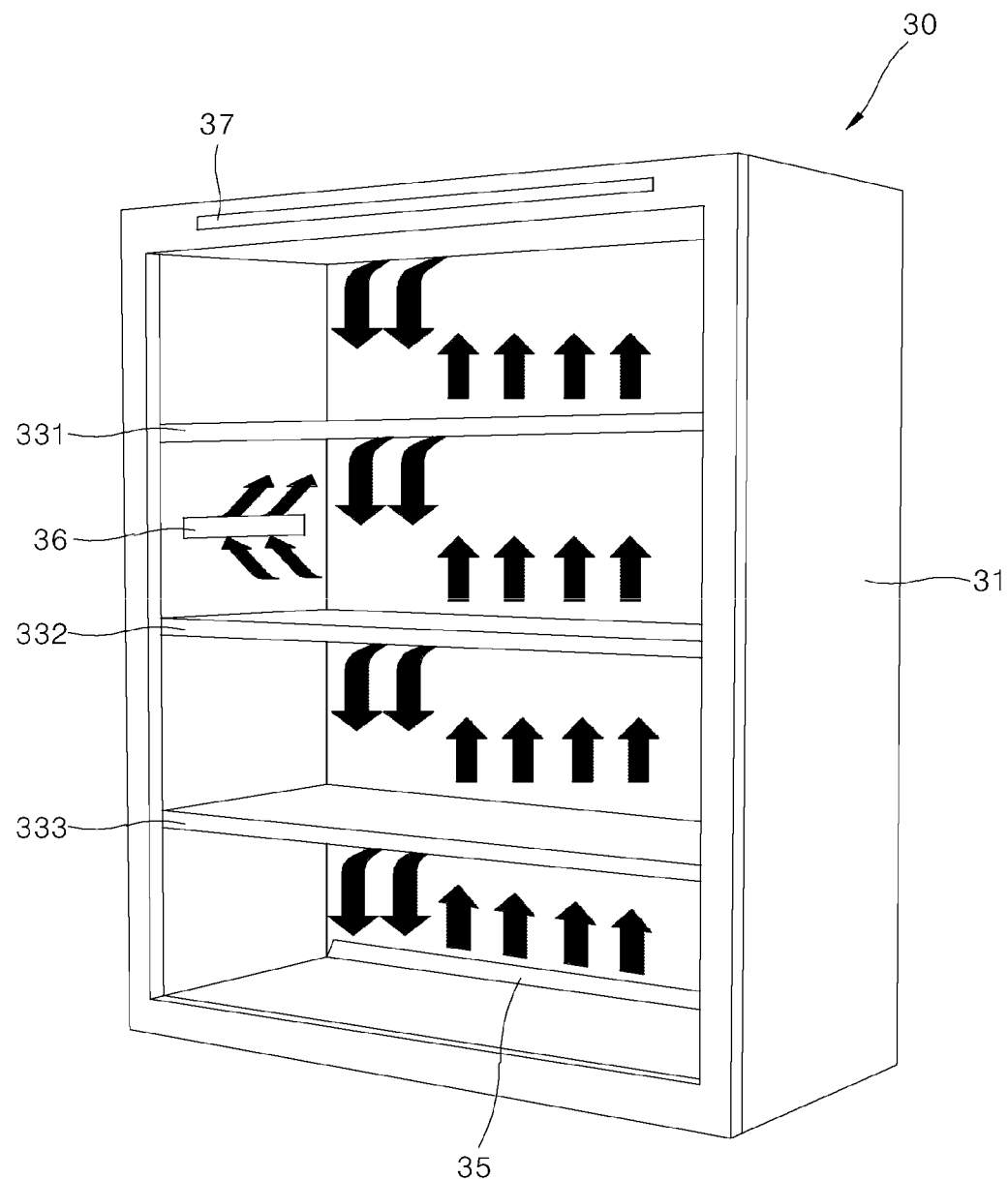
FIG. 22 is a perspective view of the second management apparatus of the shoe management apparatus according to an embodiment of the present disclosure shown in FIG. 1, with doors removed therefrom.

FIG. 22 is a perspective view of the second management apparatus 30 of the shoe management apparatus 1 according to an embodiment of the present disclosure shown in FIG. 1, with the doors removed therefrom, and is provided to illustrate circulation of air in the second management apparatus 30. In FIG. 22, arrows indicate air flow routes.

The second exhaust port 35 may be disposed at a rear bottom edge of the second cabinet 31 of the second management apparatus 30. The second exhaust port 35 may be configured to discharge air upwards therethrough.

In addition, the second exhaust port 35 may have a horizontally elongated rectangular shape. That is, the second exhaust port 35 may be narrow in width and long in length. Accordingly, air can be discharged from the second exhaust port 35 in a narrow and long shape. In this way, the air discharged from the second exhaust port 35 can more easily flow to an upper end of the second inner space IS2 defined by the second cabinet 31.

In addition, as described above, at least one of the second partitions 331, 332, 333 may be variable in angle with reference to the front-rear direction. In this way, the flow of air in the second inner space IS2 can be better circulated in the second cabinet 31.

The second cabinet 31 may include a circulation filter 36 disposed on an inner wall thereof. The circulation filter 36 may be configured to allow air to flow in from below and to flow out upwards. In an embodiment, the shoe management apparatus may further include a small fan disposed inside the circulation filter 36 to facilitate air circulation through the circulation filter 36.

The second cabinet 31 may include a front discharge port 37 formed on an upper front surface thereof. The front discharge port 37 is configured to discharge air from the second inner space IS2 to the outside of the shoe management apparatus 1 therethrough.

Figure 23:
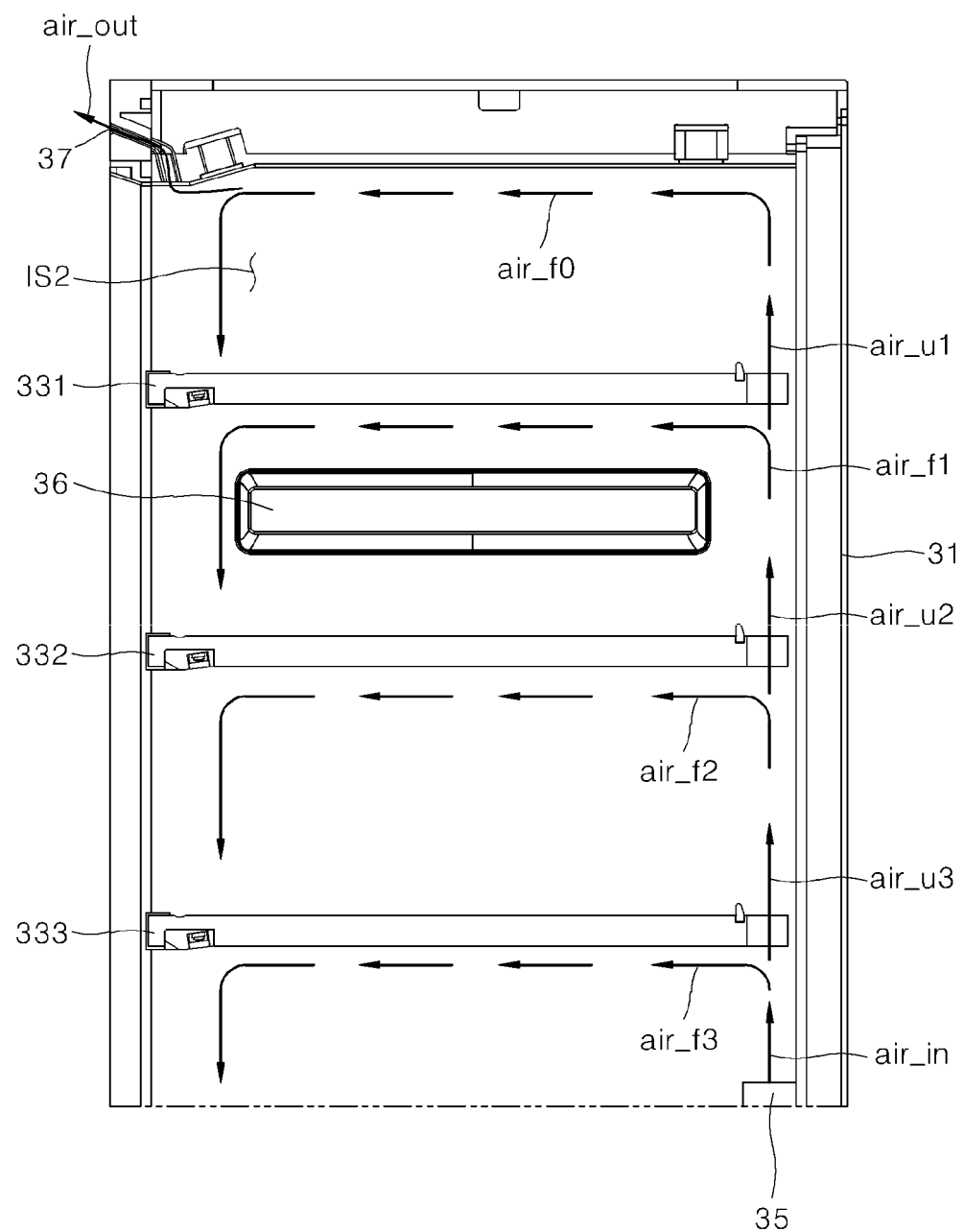
FIG. 23 is a sectional view of the second management apparatus of the shoe management apparatus according to an embodiment of the present disclosure shown in FIG. 22.

FIG. 23 is a sectional view of the second management apparatus of the shoe management apparatus according to an embodiment of the present disclosure shown in FIG. 22, illustrating air circulation in the second management apparatus 30. In FIG. 23, arrows indicate air flow routes.

At least some of the second partitions 331, 332, 333 may have a rear end at least partially spaced apart from the inner surface of the second cabinet 31.

According to an embodiment of the present disclosure, each time air (air_in) introduced into the second inner space IS2 through the second exhaust port 35 hits the rear end of each of the second partitions 331, 332, 333, some portion of the air (air_f1, air_f2, air_f3) flows forwards along a lower surface of each of the second partitions and the other portion of the air (air_u1, air_u2, or air_u3) flows upwards through a space between the rear end of each of second partitions 331, 332, 333 and the inner surface of the second cabinet 31.

In addition, among the air flowing in the second inner space defined by the second cabinet 31, air (air_u1) that has moved to an uppermost layer of the second inner space (that is, air that has passed through a space between the 1st second partition 331 and the second cabinet 31) flows forwards (air_f0) along an upper inner surface of the second cabinet 31 and then is partially discharged (air_out) to the outside of the shoe management apparatus through the front discharge port 37.

That is, according to an embodiment of the present disclosure, a point at which air is introduced into the second inner space IS2 may be diagonal to a point at which air is discharged from the second inner space IS2. More specifically, as shown in FIG. 22, air may be introduced into the second inner space IS2 through the rear lower edge of the second inner space IS2 and may be discharged from the second inner space IS2 through the front upper edge of the second inner space IS2. With this structure, air can flow over substantially the entire region of the second inner space IS2.

In addition, according to an embodiment of the present disclosure, the second exhaust port 35 may be short in the side-to-side direction and long in the front-to-rear direction, and at least some of the second partitions 331, 332, 333 may have a rear end, and at least some part of the rear end is spaced apart from the inner surface of the second cabinet 31. In this way, a larger amount of air can be moved to the upper end of the second inner space IS2.

In addition, according to an embodiment of the present disclosure, at least some of the second partitions 331, 332, 333 may be variable in angle with respect to the front-to-rear direction. In this way, air can flow in different forms in different compartments partitioned off by the second partitions 331, 332, 333, thereby improving ventilation and dehumidification efficiency.

Figure 24:
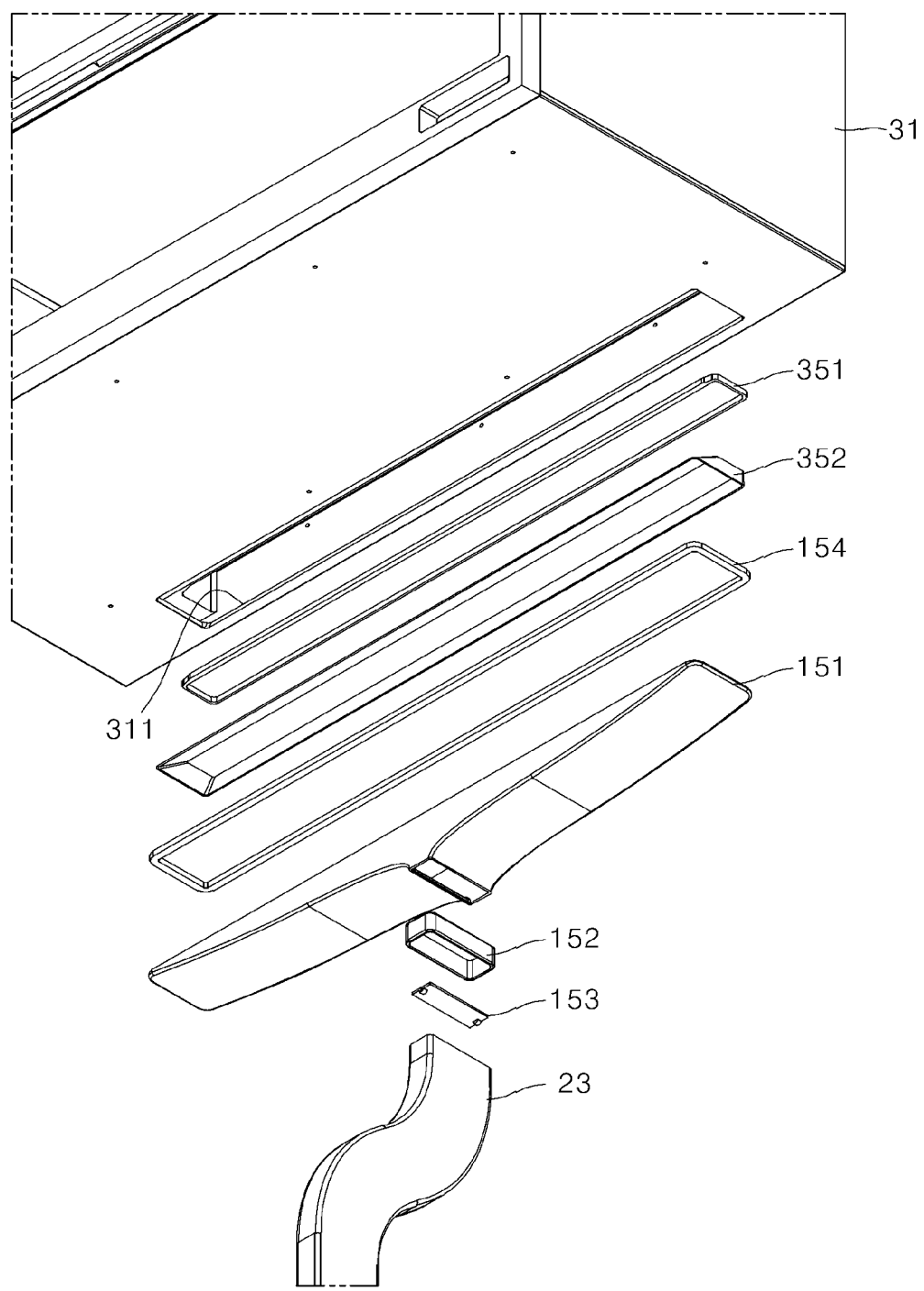
FIG. 24 is a view illustrating the configuration of a first exhaust port of the first management apparatus and a second exhaust port of the second management apparatus of the shoe management apparatus according to an embodiment of the present disclosure.

FIG. 24 shows the configuration of the first exhaust port 15 of the first management apparatus 10 and the second exhaust port 35 of the second management apparatus 30 of the shoe management apparatus according to an embodiment of the present disclosure. The first exhaust port 15 may include a diffuser 151, a first exhaust port lower packing 152, a control damper 153, and a first exhaust port upper packing 154. The second exhaust port 35 may include a second exhaust port packing 351 and a second inlet 352. In FIG. 24, reference numeral 23 denotes a longitudinal connection pipe guiding air discharged from the electric compartment (20 of FIG. 2) to the first exhaust port 15. The longitudinal connection pipe may vertically extend through the inside of the 1st first partition (131 of FIG. 2) of the first management apparatus 10.

In terms of configuration and function, the diffuser 151, the first exhaust port lower packing 152, the control damper 153, and the first exhaust port upper packing 154 may be the same as those described with reference to FIG. 10 and may be in the form of a gasket (i.e., rubber gasket, or any other material).

The second exhaust port packing 351 may be disposed between the second inlet 352 and a second bottom opening 311 formed on the bottom surface of the second cabinet 31 and configured to dispose the second exhaust port 35 therein. The second exhaust port packing 351 may be formed of an elastic material such as rubber. The second exhaust port packing 351 prevents air leakage through a gap between the second cabinet 31 and the second inlet 352 and may be in the form of a gasket (i.e., rubber gasket, or any other material). In addition, the second exhaust port packing 351 may also serve to maintain airtightness between the first exhaust port 15 (more specifically, the diffuser 151) and the second exhaust port 35 (more specifically, the second inlet 352) with the second management apparatus 30 disposed on the upper surface of the first management apparatus 10.

The second inlet 352 may be disposed at a rear bottom of the second cabinet 31. The second inlet 352 may be inserted into the second bottom opening 311 formed in the second cabinet 31. The second inlet 352 guides air delivered from the first exhaust port 15 to the second inner space IS2 defined by the second cabinet 31.

Figure 25:
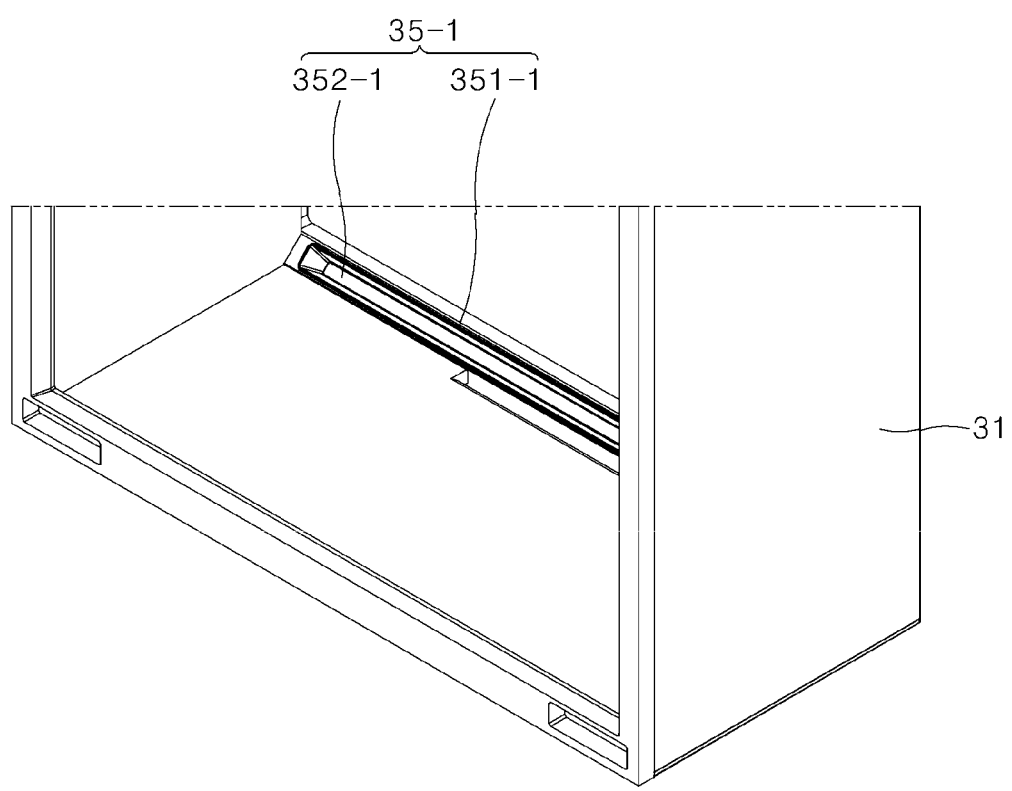
FIG. 25 shows another embodiment of the second exhaust port of the second management apparatus of the shoe management apparatus according to an embodiment of the present disclosure.

FIG. 25 shows another embodiment of the second exhaust port of the second management apparatus of the shoe management apparatus according to the present disclosure. Referring to FIG. 25, a second exhaust port 35-1 according to this embodiment may include a second duct 351-1 and a second airflow divider 352-1.

The second exhaust port 35-1 may be disposed at a rear lower edge of an interior (that is, the second inner space IS2) of the second cabinet 31.

The second duct 351-1 may be inserted into the second bottom opening 311 described above with reference to FIG. 24. The second duct 351-1 may guide air delivered from the electric compartment (20 of FIG. 3) to the second inner space IS2 and may guide air in the second inner space IS2 to the electric compartment (20 of FIG. 3).

The second airflow divider 352-1 may divide an airflow moving from the electric compartment 20 to the second inner space IS2 from an airflow moving from the second inner space IS2 to the electric compartment 20.

Figure 26:
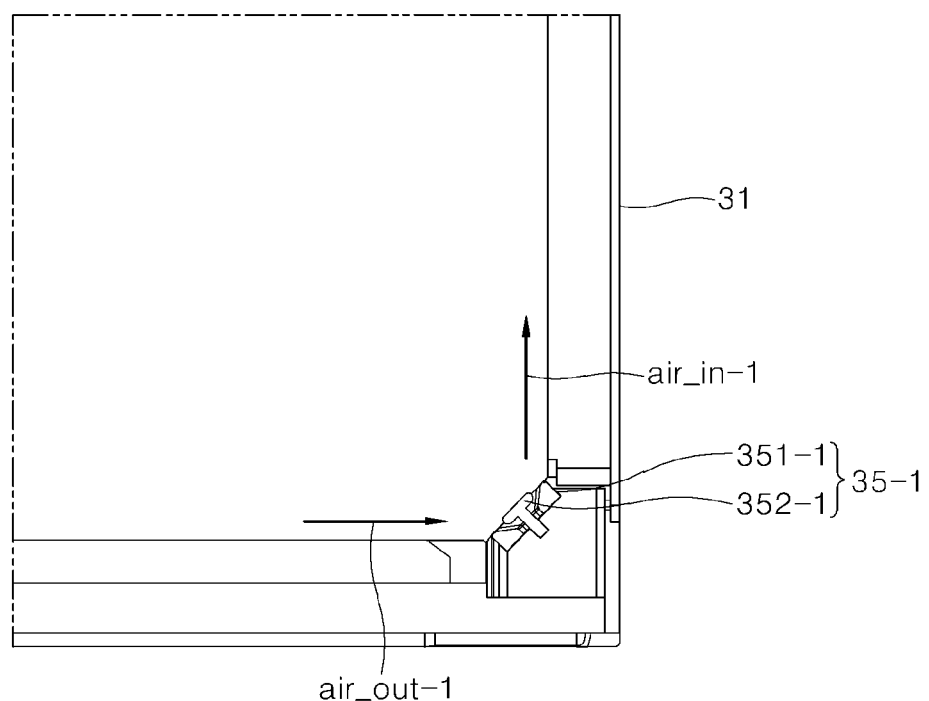
FIG. 26 is a view illustrating air flows according to the other embodiment of the second exhaust port shown in FIG. 25.

FIG. 26 is a view illustrating air flow directions according to the other embodiment of the second exhaust port shown in FIG. 25.

As described above, the second airflow divider 352-1 may divide an airflow introduced into the second inner space IS2 from an airflow discharged from the second inner space IS2. More specifically, the second airflow divider 352-1 allows airflow moving from the electric compartment 20 to the second inner space IS2 to be formed along a rear inner surface of the second cabinet 32 (air_in-1) and allows an airflow moving from the second inner space IS2 to the electric compartment 20 to be formed along a lower inner surface of the second cabinet 31 (air_out-1).

Figure 27:
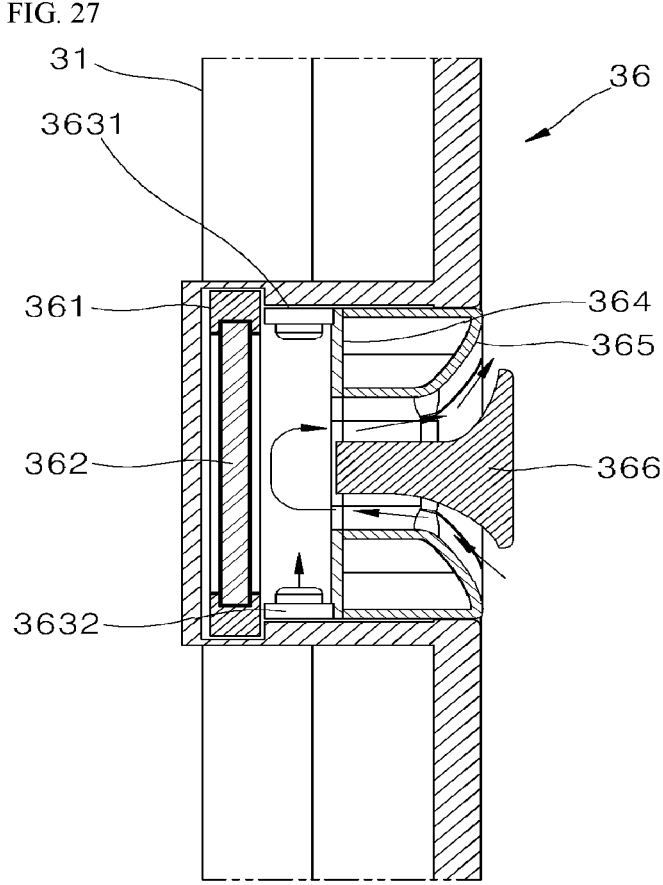
FIG. 27 is an enlarged sectional view of a circulation filter of the shoe management apparatus according to an embodiment of the present disclosure shown in FIG. 22.
Figure 28:
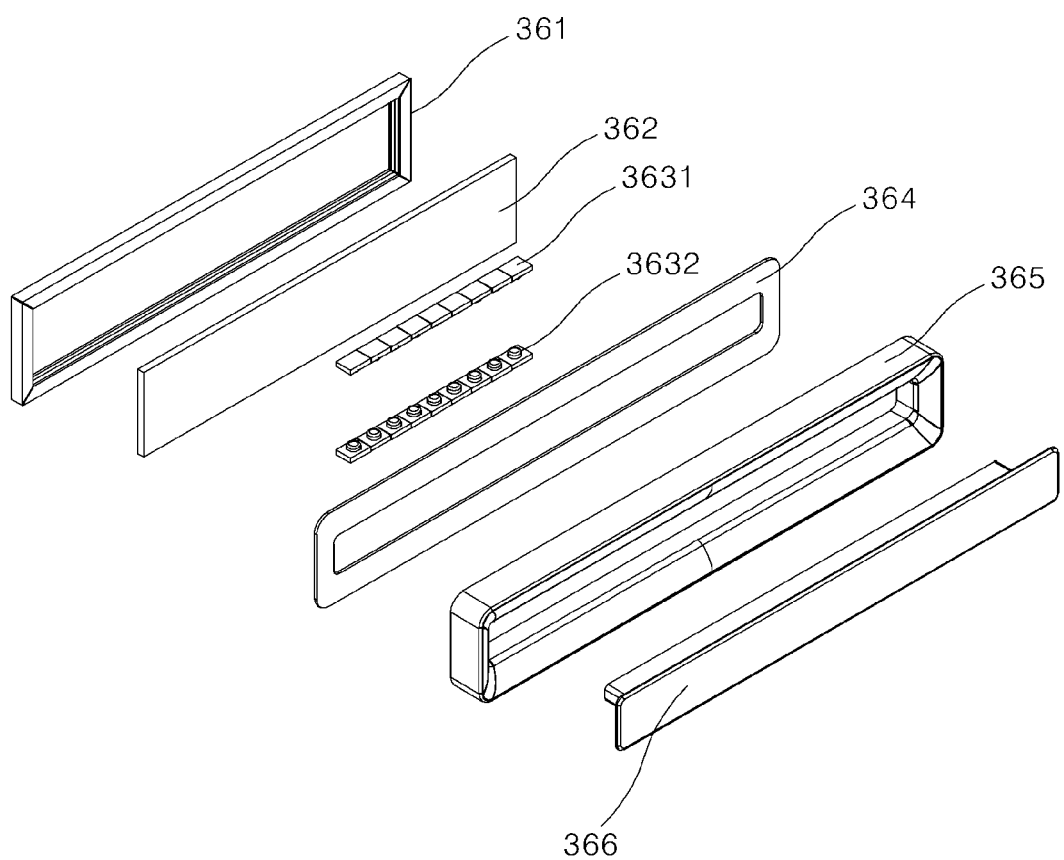
FIG. 28 is an exploded perspective view of the circulation filter of FIG. 27.

FIG. 27 is an enlarged sectional view of an embodiment of the circulation filter 36 of the shoe management apparatus 1 according to an embodiment of the present disclosure shown in FIG. 22, and FIG. 28 is an exploded perspective view of the circulation filter 36. The circulation filter 36 may include a filter frame 361, a photocatalytic filter 362, a first light source unit 3631, a second light source unit 3632, a duct-counterpart structure 364, a circulation duct 365, and an airflow deflector decoration 366. In FIG. 27, arrows indicate air flow directions.

The filter frame 361 may be inserted into an inner side surface of the second cabinet 31. That is, the second cabinet 31 may have a groove formed on the inner side surface thereof to receive the filter frame 361 therein. That is, the filter frame 361 may be inserted into the groove of the second cabinet 31. The filter frame 361 may have a hollow rectangular shape and may serve to secure the photocatalytic filter 362 thereto.

The photocatalytic filter 362 may be inserted into the filter frame 361 to be secured to the filter frame 361. The photocatalytic filter 362 may be activated by light from the first light source unit 363 and the second light source unit to remove contaminants contacting a surface thereof.

The first light source unit 3631 and the second light source unit 3632 may be disposed between the filter frame 361 and the second inner space IS2. The first light source unit 3631 and the second light source unit 3632 may be disposed to face each other. As shown in FIG. 27, the first light source unit 3631 may be disposed adjacent to an upper section of the filter frame 361 to emit light downwards, and the second light source unit 3632 may be disposed adjacent to a lower section of the filter frame 361 to emit light upwards.

The duct-counterpart structure 364 may be provided in the form of a hollow rectangle-shaped panel. The duct-counterpart structure 364 may be disposed between the second inner space IS2 and the first light source unit 3631 and the second light source unit 3632.

The circulation duct 365 may define an exterior of the circulation filter 36. The circulation duct 365 may be coupled to the duct-counterpart structure 364. In addition, the circulation duct 365 may have a horizontally symmetrical shape.

When coupled to each other, the duct-counterpart structure 364 and the circulation duct 365 may define an exterior of an air flow path.

The airflow deflector decoration 366 may be disposed at a center of the circulation duct 365. Accordingly, an air flow path can be defined between an outer surface of the airflow deflector decoration 366 and an inner surface of the circulation duct 365.

The airflow deflector decoration 366 may have a horizontally asymmetrical shape. More specifically, the airflow deflector 366 may be formed such that an air flow path defined between an upper surface of the airflow deflector decoration 366 and the circulation duct 365 has a larger area than an air flow path defined between a lower surface of the airflow deflector 366 and the circulation duct 365.

That is, according to an embodiment of the present disclosure, the circulation filter 36 has an upper opening and a lower opening, as viewed from the front. Here, the upper opening has a larger area than the lower opening. Due to this structure, the lower opening of the circulation filter 36 can serve as an air inlet and the upper opening of the circulation filter 36 can serve as an air outlet, as shown by the arrows depicted in FIG. 27. In this way, the circulation filter 36 can more appropriately use the overall flow of air in the second inner space IS2 defined by the second cabinet 31, thereby more efficiently removing contamination from the second inner space IS2.

Figure 29:
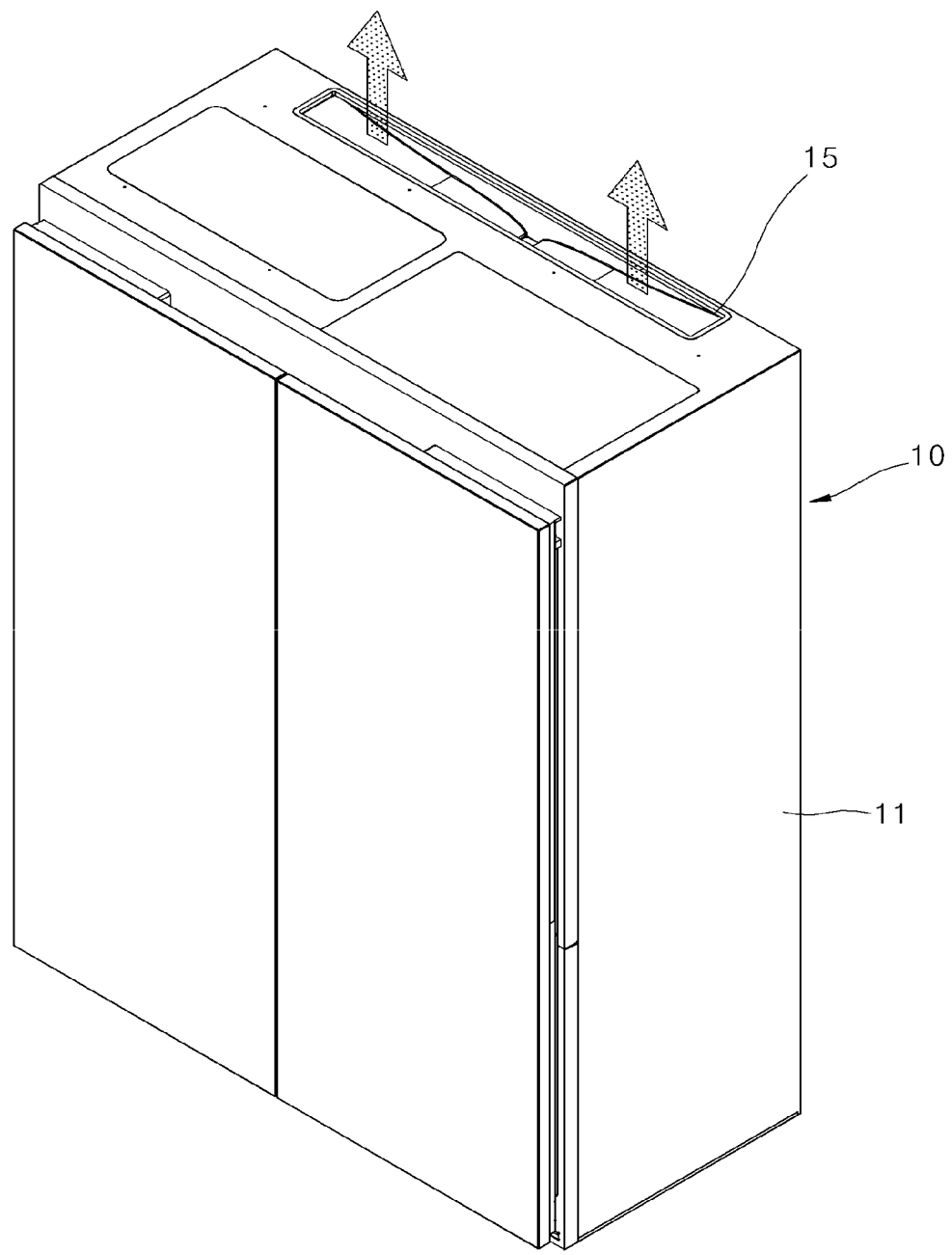
FIG. 29 is a perspective view of the first management apparatus according to an embodiment of the present disclosure.

FIG. 29 is a perspective view of the first management apparatus 10 of the shoe management apparatus 1 according to another embodiment of the present disclosure.

In this embodiment, the first management apparatus 10 may be used alone in the shoe management apparatus 1, unlike in an embodiments shown in FIG. 1 to FIG. 5. In this embodiment, the first exhaust port 15 may be used to dehumidify a space in which the shoe management apparatus 1 is installed (for example, an entrance room of a building).

Although some exemplary embodiments have been described herein, it should be understood by those skilled in the art that these embodiments are given by way of example only, and that various modifications, variations, and alterations can be made without departing from the spirit and scope of the present disclosure. In addition, although advantageous effects provided by a certain configuration are not clearly described in description of the exemplary embodiments, it should be noted that expectable effects of the corresponding configuration should be acknowledged.

What is claimed is:

1. A shoe management apparatus, comprising:
 a first management apparatus, including:
  a first inner space for storing shoes; and
  an electric compartment disposed below the first inner space, the electric compartment configured to:
   dehumidify air introduced into the electric compartment, and
   discharge dehumidified air to the first inner space to remove foreign matter from the shoes stored in the first inner space; and
 a second management apparatus disposed above the first management apparatus, including a second inner space for storing shoes, and configured to:
  receive the dehumidified air from the first management apparatus, and
  adjust humidity of the second inner space using the received dehumidified air,
 wherein air, which is supplied from the electric compartment to the first inner space, is sprayed directly toward the shoes stored in the first inner space to remove foreign matter from the shoes,
 wherein air, which is supplied from the electric compartment to the second inner space, is not sprayed directly toward the shoes, but flows inside the second inner space, and
 wherein the first management apparatus and the second management apparatus are coupled to each other so that air discharged from the electric compartment is supplied to the second management apparatus.

2. The shoe management apparatus according to claim 1, wherein the first management apparatus includes:

a first cabinet defining an exterior of the first management apparatus and defining the first inner space, the first cabinet including the electric compartment; and
a first partition extending vertically across the first inner space to divide the first inner space into a first side and a second side.

3. The shoe management apparatus according to claim 2, wherein the electric compartment includes:
a main fan configured to draw in air by creating a vacuum and discharge the drawn-in air;
a housing disposed at a first lateral side of the main fan and configured to dehumidify air therein and to allow the dehumidified air to be drawn into the main fan;
a steam generator disposed at the first lateral side of the main fan and configured to generate steam by heating water;
a water supply container disposed at a second lateral side of the main fan, opposite to the first lateral side of the main fan, to supply water to the steam generator, the water supply container being detachably coupled to the first cabinet; and
a drain container disposed at the second lateral side of the main fan to collect moisture removed in the housing.

4. The shoe management apparatus according to claim 3, wherein the electric compartment further includes an air distributor configured to:
receive the air discharged from the main fan, and distribute the received air to the first inner space and to the second inner space.

5. The shoe management apparatus according to claim 3, wherein the first management apparatus further includes:
a first exhaust port disposed at an upper surface of the first cabinet and configured to discharge air to outside of the first management apparatus; and
a longitudinal connection pipe connected between the main fan and the first exhaust port and configured to guide the air discharged from the main fan to the first exhaust port.

6. The shoe management apparatus according to claim 5, wherein the longitudinal connection pipe is at least partially disposed inside the first partition.

7. The shoe management apparatus according to claim 1, wherein the first management apparatus further includes:
an inner panel disposed at a rear portion of the first inner space with an upper end of the inner panel located further forward than a lower end of the inner panel; and
a blower fan disposed between the inner panel and an inner surface of the first cabinet and configured to force air to the first inner space.

8. The shoe management apparatus according to claim 1, wherein the first management apparatus performs at least one operation selected from contaminant removal, sterilization, deodorization, dehumidification, drying, and coating of the shoe stored in the first inner space.

9. The shoe management apparatus according to claim 1, wherein the second management apparatus includes:
a cabinet defining an exterior of the second management apparatus and defining the second inner space; and
an exhaust port disposed at a bottom surface of the cabinet and configured to receive the air discharged from the electric compartment and guide the received air to the second inner space.

10. The shoe management apparatus according to claim 9, wherein the second management apparatus further includes at least one partition extending vertically across the second inner space to divide the second inner space into a first side and a second side, and wherein the at least one partition includes a rear end at least partially spaced apart from an inner surface of the cabinet to allow air to flow between the rear end of the at least one partition and the inner surface of the cabinet.

11. The shoe management apparatus according to claim 9, wherein the second management apparatus further includes a circulation filter disposed on an inner surface of the cabinet and configured to remove contaminants from air in the cabinet.

12. A shoe management apparatus, comprising:
an electric compartment configured to:
dehumidify air introduced into the electric compartment,
generate steam by heating water, and
discharge the dehumidified air and the steam;
a first cabinet including the electric compartment and a first inner space for storing shoes disposed above the electric compartment, the first inner space being supplied with the air discharged from the electric compartment; and
a second cabinet disposed on an upper surface of the first cabinet and including a second inner space for storing shoes, the second inner space being supplied with the air discharged from the electric compartment,
wherein the steam discharged from the electric compartment is supplied only to the first inner space,
wherein the first cabinet and the second cabinet are coupled to each other so that air discharged from the electric compartment is supplied to the second inner space, and
wherein the electric compartment includes:
a main fan configured to draw in air by creating a vacuum and discharge the drawn-in air;
a housing disposed at a first lateral side of the main fan and configured to dehumidify air therein and to allow the dehumidified air to be drawn into the main fan;
a steam generator disposed at the first lateral side of the main fan and configured to generate the steam by heating water;
a water supply container disposed on a second lateral side of the main fan, opposite to the first lateral side of the main fan, to supply water to the steam generator, the water supply container being detachably coupled to the first cabinet; and
a drain container disposed at the second lateral side of the main fan to collect moisture removed in the housing.

13. The shoe management apparatus according to claim 12, further comprising:
a first exhaust port disposed at the upper surface of the first cabinet and configured to discharge air to outside of a first management apparatus; and
a second exhaust port disposed at a bottom surface of the second cabinet and configured to receive the air discharged from the electric compartment and guide the received air to the second inner space.

14. The shoe management apparatus according to claim 13, further comprising:
a first partition extending vertically across the first inner space to divide the first inner space into a first side and a second side; and
a longitudinal connection pipe at least partially disposed inside the first partition and configured to guide the air discharged from the electric compartment to the first exhaust port.

15. The shoe management apparatus according to claim 12, further comprising:
  an inner panel disposed at a rear portion of the first inner space, an upper end of the inner panel being located further forward than a lower end of the inner panel; and
  a blower fan disposed between the inner panel and an inner surface of the first cabinet and configured to force air to the first inner space.

16. The shoe management apparatus according to claim 12, further comprising a second management apparatus including at least one partition extending vertically across the second inner space to divide the second inner space into a first side and a second side, and
  wherein the at least one partition includes a rear end at least partially spaced apart from an inner surface of the second cabinet to allow air to flow between the rear end of the at least one partition and the inner surface of the second cabinet.

17. A shoe management apparatus, comprising:
  a first management apparatus, including:
    a first inner space for storing shoes; and
    an electric compartment configured to force a fluid to flow; and
  a second management apparatus disposed above the first management apparatus and including a second inner space for storing shoes, the second inner space being supplied with the fluid by the electric compartment,
  wherein the first management apparatus performs at least one operation that the second management apparatus does not perform,
  wherein the first management apparatus and the second management apparatus are coupled to each other so that air discharged from the electric compartment is supplied to the second management apparatus, and
  wherein the electric compartment includes:
    a main fan configured to draw in air by creating a vacuum and discharge the drawn-in air:
    a housing disposed at a first lateral side of the main fan and configured to dehumidify air therein and to allow the dehumidified air to be drawn into the main fan;
    a steam generator disposed at the first lateral side of the main fan and configured to generate the steam by heating water;
    a water supply container disposed on a second lateral side of the main fan, opposite to the first lateral side of the main fan, to supply water to the steam generator, the water supply container being detachably coupled to the first cabinet; and
    a drain container disposed at the second lateral side of the main fan to collect moisture removed in the housing.

18. The shoe management apparatus according to claim 17, wherein the first management apparatus performs at least one operation selected from among contaminant removal, sterilization, deodorization, dehumidification, drying, and coating for the shoes stored in the first inner space, and
  wherein the second management apparatus performs at least one operation selected from among sterilization, ventilation, and humidity control of the second inner space.

19. The shoe management apparatus according to claim 17, further comprising a fluid path extending through the first management apparatus and guiding the fluid discharged from the electric compartment to the second inner space.

* * * * *